US007045600B2

(12) United States Patent
Bank et al.

(10) Patent No.: US 7,045,600 B2
(45) Date of Patent: May 16, 2006

(54) MODIFICATION OF COLLAGENOUS MATERIALS AND MEDICAL TREATMENT, DIAGNOSIS AND MONITORING OF FIBROTIC CONDITIONS

(75) Inventors: Rudolf Antonius Bank, Hoofddorp (NL); Annemarie Jozefien van der Slot, Utrecht (NL); Anne-Marie Zuurmond, Den Haag (NL); Johannes Maria te Koppele, Leiderdorp (NL)

(73) Assignee: Nederlandse Organisatie voor Toegepastnatuur-Wetenschappelijk Ondrezoek TNO, Delft (NL)

( * ) Notice: Subject to any disclaimer, the term of this patent is extended or adjusted under 35 U.S.C. 154(b) by 365 days.

(21) Appl. No.: 10/184,372

(22) Filed: Jun. 28, 2002

(65) Prior Publication Data

US 2003/0219852 A1 Nov. 27, 2003

Related U.S. Application Data

(63) Continuation-in-part of application No. 09/450,209, filed on Nov. 29, 1999, now Pat. No. 6,733,988.

(51) Int. Cl.
*C07K 14/435* (2006.01)
*C12N 9/02* (2006.01)

(52) U.S. Cl. .................. 530/356; 435/189; 435/68.1
(58) Field of Classification Search ............... 435/68.1, 435/189; 530/356
See application file for complete search history.

(56) References Cited

OTHER PUBLICATIONS

R.A.Bank et al.; Defective Collagen Crosslinking in Bone, but not in Ligament or Cartilage, in Bruck Syndrome: Indications for a Bone-specific Telopeptide Lysyl Hydroxylase on Chromosome 17; Proc. Natl.Acad.Sci USA vol. 96, Feb. 1999, pp. 1054-1058.
R.A. Bank et al.; The Molecular Defect in/Bruck Syndrome: Evidence for Tissue-Specific Telopeptide Lysyl Hydroxylases; Official Journal of the International Bone and Mineral Society; 1998 Program and Abstracts from Second Joint Meeting; SA066, p. S543.
R.J.Fernandes et al.; Post-Translational Overmodification of Collagen Expressed by SAOS-2-Osteoblast-like Cells; 44th Annual Meeting, Orthopaedic Research Society, Mar. 16-19, 1998, p. 933.
R.A. Banks et al.; The Bruck Syndrome Evidence for Tissue-Specific Telopeptidyl Lysyl Hydroxylases; 44th Annual Meeting, Orthopaedic Research Society, Mar. 16-19, 1998; p. 324.
R.Myllylä et al.; Molecular Cloning of Chick Lysyl Hyydroxylase; The Journal of Biological Chemistry, vol. 266, No. 5, Feb. 15, 1991; pp. 2805-2810.
R. Myllylä et al.; Ascorbate Is Consumed Stoichiometrically in the Uncoupled Reactions Catalyzed by Prolyl 4-Hydroxylase and Lysyl Hydroxylase; The Journal of Biological Chemistry, vol. 259, No. 9, May 10, 1984, pp. 5403-5405.
J.Brinckmann et al.; Ehlers-Danlos Syndrome Type VI: Lysyl Hydroxylase Deficiency Due to a Novel Point Mutation (W612C),Arch Dermatol Res (1998) vol. 290; pp. 181-186.
K. Majamaa et al.; Differences Between Collagen Hydroxylases and 2-oxoglutarate Dehydrogenase in their Inhibition by Structural Analogues of 2-oxoglutarate; Biochem. J. (1985) vol. 229; pp. 127-133.
K. Kivirikko et al; Recent Developments in Posttranslational Modification: Intracellular Processing; Methods in Enzymology, vol. 144, 1987, pp. 96-114.
M.J. Barnes et al.; Hydroxylysine in the N-Terminal Telopeptides of Skin Collagen from Chick Embryo and Newborn Rat; Biochem. J. (1971) vol. 125; pp. 925-928.
M.J. Barnes et al.; Hydroxylysine in the N-Terminal Regions of $\alpha_1$ and $\alpha_2$-Chains of Various Collagens; Biochem.J., vol. 125, 1971; pp. 433-437.
R. Myllylä et al.; Modification of Vertebrate and Algal Proly 4-Hydroxylases and Vertebrate Lysyl Hydroxylase by Diethyl Pyrocarbonate; Biochem. J. vol. 286, 1992, pp. 923-927.
P.M.Royce et al.; Failure of Highly Purified Lysyl Hydroxylase to Hydoxylate Lysyl Residues in the Non-Helical Regions of Collagen; Biochem. J. vol. 230, 1985, pp. 475-480.

(Continued)

*Primary Examiner*—Charles L. Patterson, Jr.
(74) *Attorney, Agent, or Firm*—Norris McLaughlin & Marcus PA

(57) ABSTRACT

The present invention relates to the gene PLOD2 which codes for telopeptide lysyl hydroxylase (TLH). This enzyme converts telopeptidyl Lys into telopeptidyl Hyl, that can subsequently be converted into hydroxyallysine cross-links. Collagen with hydroxyallysine cross-links shows a higher resistance to degradation by proteinases than collagen with cross-links derived from allysine.

In one aspect, the invention provides methods and compositions to prepare collagenous materials with varying biodegradation rates by varying the ratio of hydroxyallysine cross-links over allysine cross-links. In another aspect, the invention provides methods and compositions to lower the ratio of hydroxyallysine cross-links over allysine cross-links in fibrotic processes, in order to obtain a collagenous network that is more easy to degrade. Furthermore, the invention provides methods to diagnose and/or monitor fibrotic processes by measuring mRNA levels of PLOD2, by measuring protein levels of the translated mRNA, and/or by measuring enzymatic activity levels of TLH. The invention also provides the description of a high through-put system facilitating the screening of antagonists of telopeptide lysyl hydroxylase.

14 Claims, 8 Drawing Sheets

OTHER PUBLICATIONS

L.Risteli et al.; Preferential Hydroxylation of Type IV Collagen by Lysyl Hydroxylase from Ehlers-Danlos Syndrome Type VI Fibroblasts; Biochemical and Biophysical Research Communications, vol. 96, No. 4 Oct. 31, 1980, pp. 1778-1784.

A.Ihrne et al.; Ehlers-Danlos Syndrome Type VI: Collagen Type Specificity of Defective Lysyl Hydroxylation in Various Tissues; The Journal of Investigative Dermatology vol. 83, No. 3, 1984, pp. 161-165.

J.Chang et al.; Urinary Pyridinoline Cross-links in Ehlers-Danlos Syndrome Type VI; Am. J. Hurn. Genet. vol. 57, 1995, pp. 1505-1508.

H.N. Yeowell et al.; Sequence Analysis of a cDNA for Lysyl Hydroxylase Isolated from Human Skin Fibroblasts from a Normal Donor: Differences from Human Placental Lysyl Hydroxylase cDNA; The Journal of Investigative Dermatology, Inc.0022-202X/94/S07.00 1994, pp. 382-384.

S. Murad et al.; Structure-Activity Relationship of Minoxidil Analogs as Inhibitors of Lysyl Hydroxylase in Cultured Fibroblasts; Archives of Biochemistry and Biophysics, vol. 292, No. 1, Jan. 1992, pp. 234-238.

J. Hanada et al.; Inhibition of Cultured Human RPE Cell Proliferation and Lysyl Hydroxylase Activity in Hydroxy Derivatives of Minoxidil; Investigative Ophithalmology & Visual Science, vol. 35, No. 2, Feb. 1994, pp. 463-469.

J. Handa et al.; Minoxidil Inhibits Ocular Cell Proliferation and Lysyl Hydroxylase Activity; Investigative Ophithalmology & Visual Science, vol. 34, No. 3 Mar. 1993, pp. 567-575.

T. Hautala et al.; Minoxidil Specifically Decreases the Expression of Lysine Hydroxylase in Cultured Human Skin Fibroblasts; Biochem. J. vol. 283, 1992, pp. 51-54.

K. Passoja et al.; Identification of Arginine-700 as the Residue That Binds the C-5 Carboxyl Group of 2-Oxoglutarate in Human Lysyl Hydroxylase 1; Federation of European Biochemical Societies Letters 434, 1998, pp. 145-148.

T. Hautala et al.; Cloning of Human Lysyl Hydroxylase: Complete cDNA-Derived Amino Acid Sequence and Assignment of the Gene (PLOD) to Chromosome 1p36.6-p36.2; Genomics 13, 1992, pp. 62-69.

K. Passoja et al.; Cloning and Characterization of a Third Human Lysyl Hydroxylase Isoform; Proc. Natl. Acad. Sci, USA, vol. 95, Sep. 1998, pp. 10482-10486.

M. Valtavaara et al.; Cloning and Characterization of a Novel Human Lysyl Hydroxylase Isoform Highly Expressed in Pancreas and Muscle; The Journal of Biological Chemistry, vol. 272, No. 11, Mar. 14, 1997, pp. 6831-6834.

A. Pirskanen et al.; Site-directed Mutagenesis of Human Lysyl Hydroxylase Expressed in Insect Cells; The Journal of Biologifal Chemistry, vol. 271, No. 16, Apr. 19, 1996, pp. 9398-9402.

M. Valtavaara et al.; Primary Structure, Tissue Distribution, and Chromosomal Localization of a Novel Isoform of Lysyl Hydroxylase (Lysyl Hydroxylase 3); The Journal of Biological Chemistry, vol. 273, No. 21, May 22, 1998, pp. 12881-12886.

B. Krol et al.; The Expression of a Functional, Secreted Human Lysyl Hydroxylase in a Baculovirus System; The Journal of Investigative Dermatology, Inc., 0022-202X/96, 1996, pp. 11-16.

J. Gerriets et al.; Tendon Hypertrophy is Associated witH Increased Hydroxylation of Nonhelical Lysine Residues at Two Specific Cross-linking Sites in Type 1 Collagen; The Journal of Biological Chemistry, vol. 268, No. 34, Dec. 5, 1993, pp. 25553-25560.

L. Forrest et al.; A comparison Between the Reducible Intermolecular Crosslinks of the Collagens from Mature Dermis and Young Dermal Scar Tissue of the Guinea Pig; Biochemical and Biophysical Research Communications, vol. 46, No. 5, 1972, pp. 1776-1781.

D. Cannon et al.; Collagen Cross-linking in Corneal Scar Formation; Biochimica et Biophysica Acta. 412 (1975) pp. 18-25.

K. Reiser et al.; A Molecular Marker for Fibrotic Collagen in Lungs of Infants with Respiratory Distress Syndrome; Biochemical Medicine and Metabolic Biology, vol. 37, 1987; pp. 16-21.

J. Last et al.; Hydroxylation of Collagen by Lungs of Rats Administered Bleomycin; American Journal of Respiratory Cell and Molecular Biology, vol. 2, 1990, pp. 543-548.

J. Last et al.; Collagen Cross-linking in Adult Patients with Acute and Chronic Fibrotic Lung Disease; Department of Internal Medicine, School of Medicine and California Primate Research Center, Univeristy of California, et al.; Mar. 14, 1989, pp. 307-313.

T. Moriguncbi et al.; Crosslink of Collagen in Hypertrophic Scar; The Journal of Investigative Dermatology, vol. 72, 1979, pp. 143-145.

S. Ricard-Blum et al.; Mechanism of Colllagen Network Stabilization in Human Irreversible Granulomatous Liver Fibrosis; Gastroenterology, vol. 111, 1996, pp. 172-182.

A. Bailey et al.; Intermolecular Cross-linking in Fibrotic Collagen; AFRC Food Research Institute; pp. 80-96.

k.Uzawa et al.; Altered Posttranslational Modifications of Collagen in Keloid; Biochemical and Biophysical Research Communications, vol. 249, 1998, pp. 652-655.

S. Ricard-Blum et al.; Hydroxypyridinium Collagen Cross-links in Human Liver Fibrosis: Study of Alveolar Echinococcosis; Hepatology, 1991, pp. 599-602.

J. Gerriets et al.; Lung Collagen Cross-links in Rats with Experimentally Induced Pulmonay Fibrosis; Biochimica et Biophysica Acta, vol. 1316, pp. 121-131.

J. Brinckman et al.; Altered X-ray Diffraction Patterns is Accompanied by a Change in the Mode of Cross-link Formation in Lipodermatosclerosis; The Journal for Investigative Dermatology, Inc., 0022-202X/96, 1996, pp. 589-592.

L. Knott et al.; Collagen Cross-links in Mineralizing Tissues: A Review of Their Chemistry, Function, and Clinical Relevance; Elsevier, Bone vol. 22, No. 3, Mar. 1998, pp. 181-187.

M. Pasquali et al; Abnormal Formation of Collagen Cross-links in Skin Fibroblasts Cultured from Patients with Ehlers-Danlos Syndrome Type VI; Proceedings of the Association of American Physicians, vol. 109, No. 1, pp. 33-41.

S. Ricard-Blum et al.; Pyridinoline, a Mature Collagen Cross-link, in Fibrotic Livers from *Schistosoma mansoni*-Infected Mice; Am. J. Trop. Med. Hyg., No. 47(6), 1992, pp. 816-820.

S. Ricard-Blum et al.; Covalent Cross-linking of Liver Collagen by Pyridinoline Increases in the Course of Experimental Alveolar Echinococcosis; Parasite, vol. 2 1995, pp. 113-118.

S. Ricard-Blum et al.; The Level of the Collagen Cross-link Pyridinoline Reflects the Improvement of Cutaneous Lesions in One Case of Skin Alveolar Echinococcosis; Parasitol Res, 1998, vol. 84, pp. 715-719.

S. Ricard-Blum et al.; Collagen Cross-linking by Pyridinoline Occurs in Non-reversible Skin Fibrosis; Cellular and Molecular Biology vol. 39(7), 1993, pp. 723-727.

K. Uzawa et al.; Differential Expression of Human Lysyl Hydroxylase Genes, Lysine-Hydroxylation, and Cross-linking of Type I Collagen During Osteoblastic Differentiation in Vitro; Journal of Bone and Mineral Research; vol. 14, No. 8, 1999, pp. 1272-1280.

S. Robins; Fibrillogenesis and Maturation of Collagens; Dynamics of Bone and Cartilage Metabolism, 1999 Academic Press; pp. 31-42.

J. Last et al.; Biosynthesis of Collagen Crossllinks. III. *In Vivo* Labeling and Stability of Lung Collagen in Rats with Bleomycin-induced Pulmonary Fibrosis; American Journal of Respiratory Cell and Molecular Biology, vol. 1, 1989, pp. 111-117.

K. Reiser et al.; Changes in Collagen Cross-linking in Bleomycin-induced Pulmonary Fibrosis; Journal of Biochemical Toxicology 1, 1986, pp. 83-91.

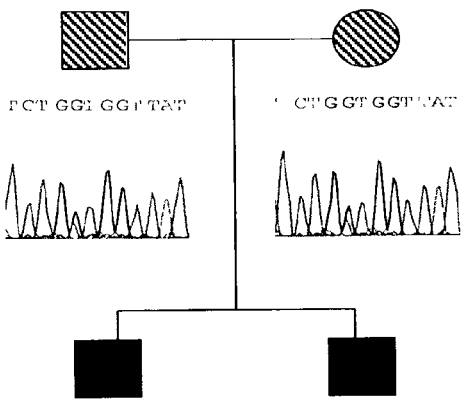
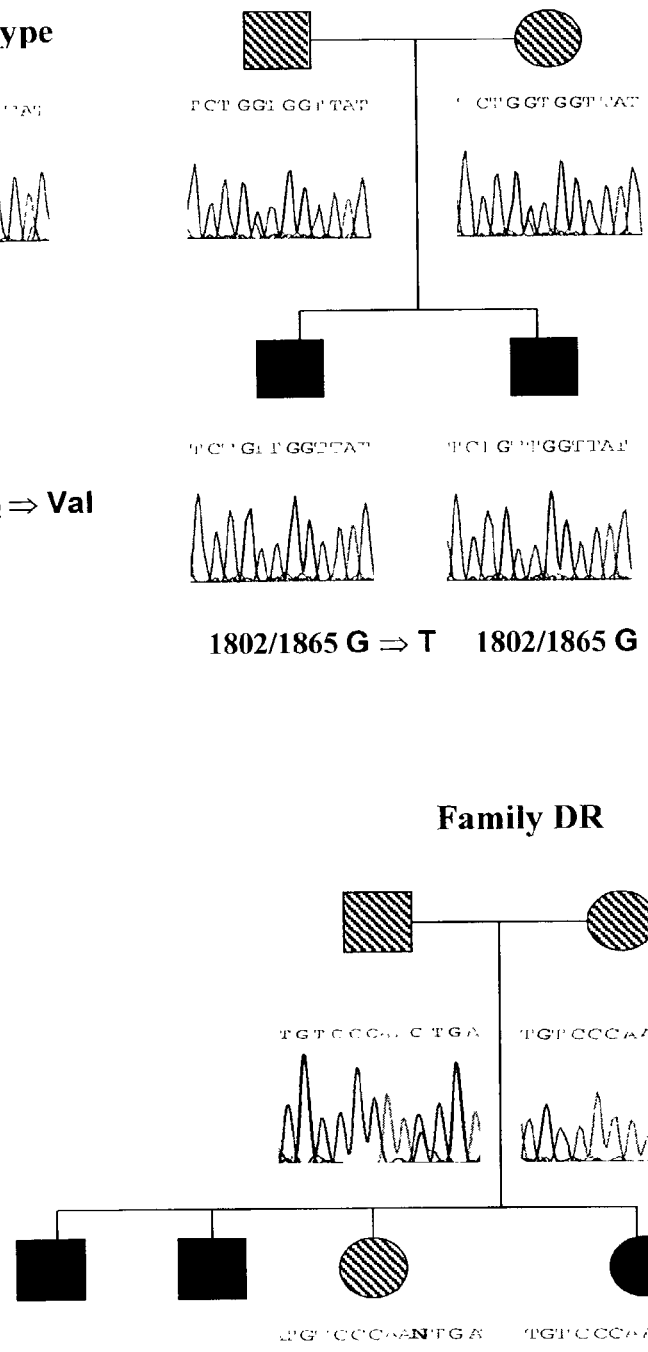
Figure 3
Figure 4

MODIFICATION OF COLLAGENOUS MATERIALS AND MEDICAL TREATMENT, DIAGNOSIS AND MONITORING OF FIBROTIC CONDITIONS

This application is a continuation-in-part application of U.S. Ser. No. 09/450,209 filed Nov. 29, 1999 now U.S. Pat. No. 6,733,988.

FIELD OF THE INVENTION

This invention is in the general field of modifying collagenous materials in order to increase or decrease their stability towards enzymatic degradation (in particular by proteinases). Furthermore, the invention is in the field of medical treatment of fibrotic conditions, and in the fields of diagnosis and/or monitoring of fibrotic processes. Furthermore, the invention is in the field of screening tests for substances that are potentially useful in the treatment of fibrotic conditions.

BACKGROUND OF THE INVENTION

Fibrillar collagens (e.g. collagen type I, II, III, V and XI) consist of a triple helical domain, flanked by telopeptides at both the aminoterminal and carboxyterminal end of the molecule (N-telopeptide and C-telopeptide, respectively). Biosynthesis of collagen is a multistep process, resulting in modifications of both the triple helix and the telopeptides. One of the steps in the biosynthesis of collagen is hydroxylation of certain lysine residues in the triple helix and telopeptides by the enzyme lysyl hydroxylase (EC 1.14.11.4).

Extracellular collagen molecules aggregate spontaneously into microfibrils. Further stabilization of the molecules occurs by means of cross-links. Cross-linking is initiated by conversion of specific lysine (Lys) or hydroxylysine (Hyl) residues of the telopeptides into the aldehydes allysine and hydroxyallysine, respectively, by the enzyme lysyl oxidase (EC 1.4.3.13) [H. M. Kagan, 1994, Path. Res. Pract., 190: 910–919]. The aldehydes subsequently react with Lys or Hyl residues in the triple helix to give characteristic di-functional cross-links. These cross-links eventually mature into tri- or tetra-functional cross-links [D. R. Eyre, 1987, Meth. Enzymol., 144: 115–139; A. J. Bailey et al., 1998, Mech. Ageing Developm, 106: 1–56].

Two related routes for the formation of cross-links have been described, one based on allysine from the telopeptides, the other based on hydroxyallysine from the telopeptides. Each route results in chemically distinct cross-links. Examples of the hydroxyallysine cross-links are hydroxylysylpyridinoline (HP) and lysylpyridinoline (LP); the precursors of these cross-links are di-functional cross-links known in their reduced form as dihydroxylysinonorleucine (DHLNL) and hydroxylysinonorleucine (HLNL), respectively.

It is well known that the stability of collagen molecules in environments containing proteinases depends, amongst others, on the level of cross-linking. The stability of collagen molecules against proteinases can be enhanced by increasing the amount of cross-links. Cross-links can be enzymatically mediated cross-links and non-enzymatically mediated cross-links. The enzymatically mediated cross-links are generated by lysyl oxidase. Introduction of cross-links in a non-enzymatic way can be achieved by treating collagen with a variety of chemicals, such as aldehydes, epoxides, isocyanates, acyl azides, carbodiimides, reducing sugars (the so-called Maillard reaction), or by a variety of physical methods, such as irradition (e.g. short-wave UV irradiation) or dehydrothermal treatments. There is an extensive amount of literature and patents dealing with controlling the biodegradation time of collagen by means of enhancing collagen cross-linking by lysyl oxidase, chemicals or physical methods. Controlling the degradation time of collagenous materials is highly important, especially in the field of drug release and tissue engineering. The starting point to engineer a tissue is the design of a scaffold and a consideration of the kind of cells to be seeded into the scaffold. Scaffolds can also be used in various wound healing situations. Biodegradation of scaffolds is required to prevent longterm physical hindrance of the implant. The rate of degradation is dependent on the application and has to be in concert with tissue formation. Collagen is often used as a basis for the manufacturing of scaffolds. For a number of applications, non-crosslinked collagen cannot be used because of its susceptibility to decomposition by metalloproteinases before it can be remodelled into a resistant replacement. In such cases, a collagen scaffold is needed showing higher resistancies toward proteinases. Therefore, various methods have been developed to control the speed of degradation of collagen, such as the above mentioned chemical and physical methods.

A disadvantage of chemical and physical methods is that the position of the cross-links within the molecule cannot be controlled: cross-links are generated throughout the molecule. In addition, said cross-links can be intramolecular or intermolecular. Another disadvantage is that most chemical and physical methods partially denature the collagen molecules: denatured collagen is highly susceptible to proteolytic degradation. Other disadvantages are that certain cross-links show some toxicity, have immunogenic properties, adversity affect biomechanical properties, adversity affect cell/matrix interactions, or that the treatment enhances unwanted side-effects, such as calcification of the matrix.

These problems can be overcome by using lysyl oxidase: the formed aldehydes react with amino acids located at very specific positions within the triple helix. Furthermore, because the cross-links normally occur in vivo, the cross-links do not show toxicity or immunogenicity, and the treatment with lysyl oxidase does not result in a denaturation of collagen molecules.

In some cases, the durability of collagen molecules cross-linked by means of lysyl oxidase in proteolytic environments is not high enough, resulting in biodegradation times that are too short. In other cases, collagen cross-linked by lysyl oxidase show biodegradation times that are too long. The latter is for example the case in fibrosis. In fibrotic conditions an unwanted accumulation is seen of collagen molecules that is difficult to degrade by proteinases.

SUMMARY OF THE INVENTION

A need exists for tools controlling the biodegradation time of collagenous materials based on the formation of naturally occurring cross-links. Here we show that collagen cross-linked by hydroxyallysine cross-links is more resistant toward proteolytic enzymes and more difficult to degrade than collagen cross-linked by allysine. Both cross-links occur in vivo and are generated by lysyl oxidase. Our approach is unique in that it controls the biodegradation time of collagens by controlling the lysyl hydroxylation level of the telopeptides. This is achieved by controlling the levels of telopeptide lysyl hydroxylase, the enzyme that hydroxylates the lysine residues located in the telopeptides.

The present invention also relates to the observation that the amount of hydroxyallysine cross-links is enhanced in fibrotic tissues, explaining in part the irreversibility of collagen accumulation in fibrosis.

Here we also show that the gene PLOD2 encodes a telopeptide lysyl hydroxylase, making it possible to regulate the lysyl hydroxylation level of the telopeptides. Previously, it was not known whether the enzyme encoded by PLOD2 hydroxylates the Lys in the telopeptides or the Lys in the triple helix of the collagen.

The invention has a broad applicability: it can be used for the preparation of collagenous materials used in tissue engineering or drug delivery but also in the field of medical treatments aimed at inhibiting fibrotic processes. In fibrotic tissues, a switch is seen in the telopeptide-lysyl-crosslink pathway toward the telopeptide-hydroxylysyl-crosslink pathway. Inhibition of the synthesis (transcription, translation) of the enzyme encoded by PLOD2 and/or inhibition of the enzymatic activity of the PLOD2-encoded protein results in a collagen network that is predominantly cross-linked by means of allysine cross-links, a network that is more easy to degrade by proteinases. The subject invention also concerns new materials and methods for the detection of fibrotic processes based on the novel finding that the gene PLOD2 encodes telopeptide lysyl hydroxylase and that this enzyme plays a key role in fibrosis.

The present invention provides methods for the preparation of collagenous materials exhibiting variable degradation times in environments containing proteolytic enzymes, based on modifying the hydroxylysine levels in the telopeptides.

The present invention provides a new method for selectively inhibiting the formation of hydroxyallysine cross-links, but not allysine-derived cross-links in wound healing and in other processes in which fibrosis occurs, thus increasing the proteolytic degradation rate of the assembled collagen network. The selectivity of the method is such that biosynthesis of allysine cross-links will not be compromised, thus resulting in collagen with favourable mechanical properties over non-cross-linked collagen. This specificity can be achieved by administration of an effective amount of a composition that selectively inhibits the activity or production of telopeptide lysyl hydroxylase but not lysyl oxidase.

The subject invention furthermore concerns methods for estimating or determining the amount of mRNA copies transcribed from the PLOD2 gene as a means to monitor the onset and/or the progression of fibrosis/scarring. The invention further provides methods for measuring the amount of PLOD2-encoded enzyme in a sample by means of antibodies and/or aptamers or other means, and methods for determining telopeptide lysyl hydroxylase activity levels in a sample using one or more hydroxylatable sequences. Said methods are tools to diagnose or monitor fibrotic processes.

Additionally, the invention provides methods for measuring telopeptide lysyl hydroxylase activity in a test system designed to screen compounds exhibiting inhibitory properties towards the activity of the enzyme or antagonist properties with respect to the transcription of the PLOD2 gene or the translation of the respective RNA template.

Further objects and advantages of the invention with respect to compositions capable of suppressing or repressing the synthesis (transcription and/or translation) of telopeptide lysyl hydroxylase and/or compounds capable of inhibiting the activity of said enzyme will be clear to one skilled in the art upon consideration of the following detailed description.

Examples demonstrate (1) that collagen cross-linked by allysine is easier to degrade by proteinases than collagen cross-linked by hydroxyallysine, (2) various mutations of the PLOD2 gene in Bruck syndrome, showing that PLOD2 is a telopeptide lysyl hydroxylase, (3) that increased PLOD2 expression levels result in increased hydroxyallysine cross-link levels, (4) methods to measure mRNA levels of PLOD2, (5) that expression of PLOD2 is highly increased in myofibroblasts, cells that mediate fibrosis, (6) formats of a high through-put assay designed to screen compounds exhibiting inhibitory properties towards telopeptide lysyl hydroxylase, (7) methods to prepare collagenous materials with varying degradation rates, (8) methods to increase telopeptide lysyl hydroxylase levels in cells in order to obtain collagen with high lysyl hydroxylation levels in the telopeptides, (9) methods to inhibit telopeptide lysyl hydroxylase in order to obtain collagen with low lysyl hydroxylation levels in the telopeptides.

BRIEF DESCRIPTION OF THE DRAWINGS

FIG. 3 is a graph showing the missense mutation found in Bruck syndrome family PM, resulting in a Gly→Val mutation in the sequence GGYENVPT (SEQ ID NO: 1) (the mutated residue is underligned).

FIG. 4 is a graph showing the missense mutation found in Bruck syndrome family DR, resulting in a Thr→Ile mutation in the sequence GGYENVPT (SEQ ID NO: 1) (the mutated residue is underligned). Both FIGS. 3 and 4 provide direct evidence that PLOD2 encodes telopeptide lysyl hydroxylase.

DETAILED DESCRIPTION OF THE INVENTION

Figure 1:
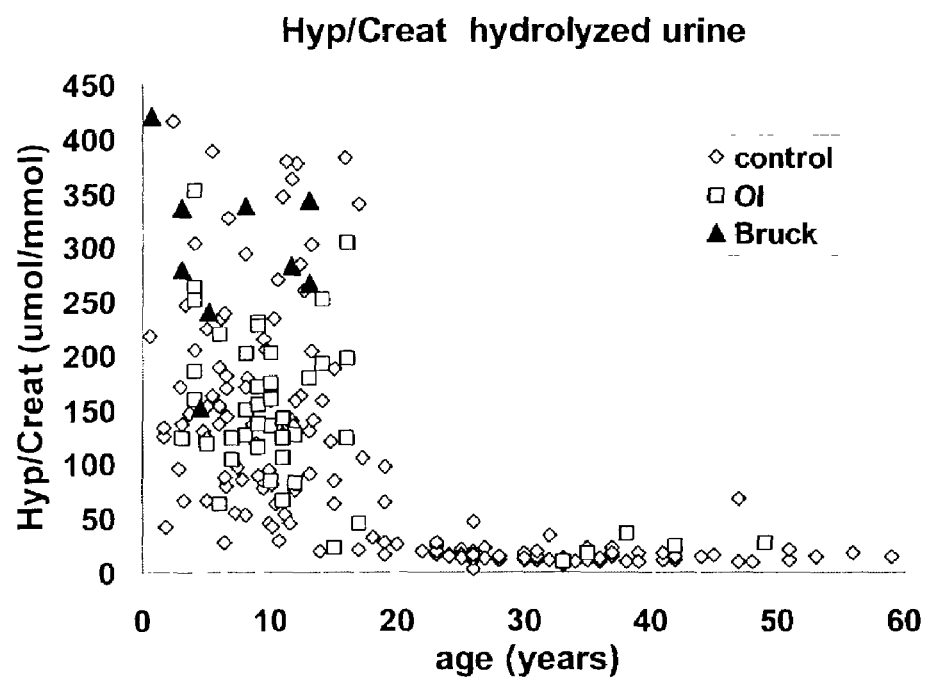
FIG. 1 shows the graphs depicting (A) the level of collagen degradation products (Hyp=hydroxyproline) as well as (B) the hydroxyproline to proline (Hyp:Pro) ratio in Bruck syndrome urine, compared to urine from healthy subjects and urine from osteogenesis imperfecta (OI) patients. The data indicate that the degradation of bone collagen in Bruck syndrome, which is characterized by the almost complete absence of hydroxyallysine cross-links, is significantly elevated.
Figure 1:
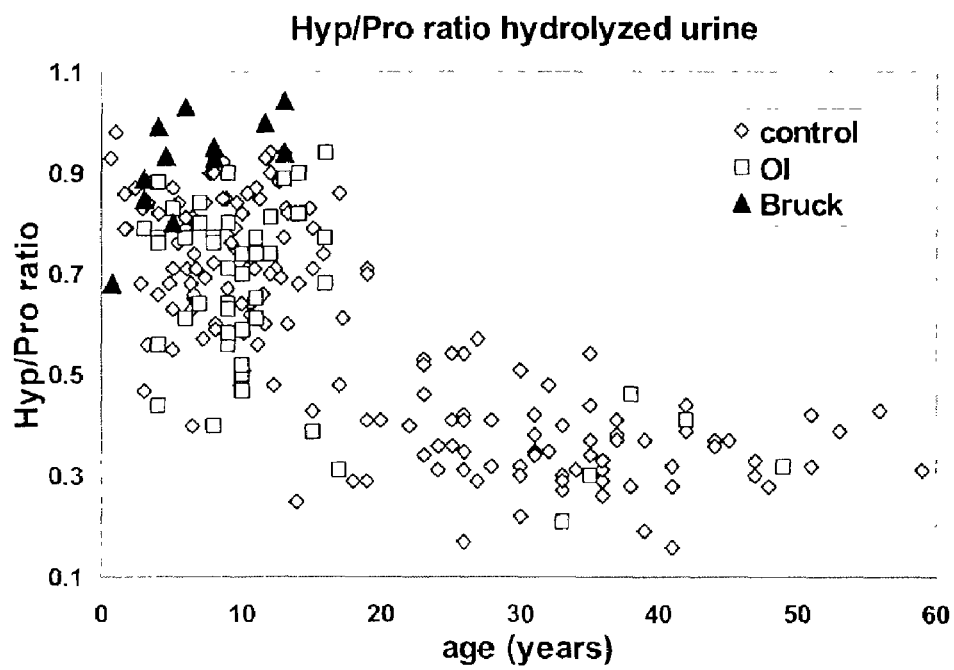

The invention provides a method for obtaining a collagenous matrix which comprises cross-linked collagen molecules wherein the resistance of said collagenous matrix against proteolytic degradation is controlled by controlling the ratio of hydroxyallysine cross-links to allysine cross-links in the collagenous matrix. The ratio of hydroxyallysine cross-links to allysine cross-links in the collagenous matrix may be controlled by controlling the lysyl hydroxylation level of the collagen telopeptides. The lysyl hydroxylation level of the collagen telopeptides may be controlled by controlling the level of telopeptide lysyl hydroxylase activity. The level of telopeptide lysyl hydroxylase activity may be controlled by controlling the expression of a PLOD2 gene or by controlling the telopeptide lysyl hydroxylase activity of a PLOD2 expression product. Preferably, the level of telopeptide lysyl hydroxylase activity is controlled without simultaneously affecting helical lysyl hydroxylase activity, although a simultaneous increase or decrease of helical lysyl hydroxylase activity may be accepted. More preferably, the level of telopeptide lysyl hydroxylase activity is controlled in such a way that lysyl oxidase activity is not affected. Thereby, the invention allows to achieve a modified ratio of hydroxyallysine cross-links to allysine cross-links in the collagenous matrix without significantly affecting the overall degree of cross-linking.

The invention comprises methods which are carried out in vitro, in particular methods for producing a collagenous matrix with a desirable resistance against proteolytic degradation or breakdown, i.e. a desirable biodegradation time, in particular a desirable high or low stability against proteolytic degradation. Such in vitro methods may involve the use of living cells for producing collagen, but may also be completely cell-free. The invention further comprises methods carried out in vivo, i.e. in living mammals, in particular in human beings, wherein a major application is in a treatment of fibrotic conditions.

Furthermore, the invention provides a method for diagnosing and/or monitoring the occurrence or state of a fibrotic process in a mammal comprising taking a sample (in particular a tissue sample) from said mammal, analyzing said sample to determine the expression level of a PLOD2 gene and comparing said expression level with a standard.

The invention also provides an assay (in particular a high-troughput assay) for screening compounds or compositions to determine their effect on telopeptide lysyl hydroxylase activity comprising contacting under enzymatically functional conditions a compound or composition to be tested with a PLOD2-encoded telopeptide lysyl hydroxylase enzyme and a suitable substrate for this enzyme, and determining the level of lysyl hydroxylation of the substrate compared to the level of lysyl hydroxylation of the substrate in the absence of the compound or composition to be tested. Such assay preferably further comprises separating, after said contacting of the compound or composition to be tested with a PLOD2-encoded telopeptide lysyl hydroxylase enzyme and suitable substrate for it, the substrate from the reaction mixture, reacting the substrate successively with an oxidizing agent, such as periodate, which is capable of oxidizing the hydroxyl group of Hyl to an aldehyde moiety, and a hydrazide dye, and measuring the fluorescence from the substrate.

Further, the invention provides an assay for screening compounds or compositions to determine their effect on telopeptide lysyl hydroxylase expression comprising growing cells expressing a PLOD2-encoded telopeptide lysyl hydroxylase enzyme in the presence of a compound or composition to be tested and determining the level of PLOD2 expression compared to the level of PLOD2 expression in the absence of the compound or composition to be tested.

Definitions

Telopeptide lysyl hydroxylase refers to an enzyme that is capable of converting lysine residues of collagen telopeptides into hydroxylysine. As opposed to helical lysyl hydroxylase, telopeptide lysyl hydroxylase has a higher affinity for Lys located in the telopeptides than Lys located in the triple helical part of the collagen molecule.

In this invention, the term telopeptide lysyl hydroxylase refers to the biologically active enzyme encoded by the nucleic acid sequence of the PLOD2 gene, or a nucleic acid sequence homologous to it. Said enzyme is derived from the complete mRNA sequence of PLOD2, a splice variant thereof, or a fragment of the PLOD2 nucleic acid sequence (but still encoding a polypeptide displaying biological activity in the sense that it hydroxylates lysine residues in the telopeptides). The invention also encompasses PLOD2 variants, i.e. differing in nucleotide sequence or even in amino acid sequence of the encoded polypeptide, but still encoding a polypeptide displaying activity in the hydroxylation of lysine residues in the telopeptides. Several PLOD2 variants are known in the art. A preferred PLOD2 variant is one having at least 90% amino acid sequence identity to the PLOD2 amino acid sequence. As a result of the degeneracy of the genetic code, a multitude of polynucleotide sequences encoding telopeptide lysyl hydroxylase, some bearing minimal homology to the polynucleotide of PLOD2, may be produced. Thus, the invention contemplates each and every possible variation of polynucleotide sequences that could be made by selecting combinations based on possible codon choices.

Some examples of known PLOD2 sequences can be found in M. Valtavaara et al. (1997, J. Biol. Chem., 272 (11): 6831–6834), H. N. Yeowell & L. C. Walker (1999, Matrix Biology, 18: 179–187), H. Ruotsalainen et al. (1999, Matrix Biology, 18: 325–329), and H. Ruotsalainen et al. (2001, Matrix Biology, 20: 137–146). Said publication by Yeowell & Walker described the presence of two splice variants of PLOD2. In this patent application, PLOD2A refers to the short form, whereas PLOD2B refers to the form of PLOD2 containing exon 13A (located between exon 13 and exon 14).

The words "inhibits the activity or production of telopeptide lysyl hydroxylase" are used herein in a broad sense, in that they not only cover the actual inhibition of the enzyme as such, but also cover an inhibition of the transcription of the telopeptide lysyl hydroxylase gene, inhibition of the translation of mRNA derived from the telopeptide lysyl hydroxylase gene, and treatment with (a recombinant gene coding for) a mutated telopeptide lysyl hydroxylase or a fragment thereof that shows no activity towards telopeptides but that is competitive to endogenous telopeptide lysyl hydroxylase with respect to its natural substrate (collagen telopeptides).

The term "antagonist" as it is used herein, refers to a molecule which decreases the amount or duration of the effect of the biological activity of telopeptide lysyl hydroxylase. Antagonists may include proteins, nucleic acids, carbohydrates, antibodies, aptamers, or any other molecules which decrease the effect of telopeptide lysyl hydroxylase.

Fibrosis is a disorder or undesirable physical condition characterized by excessive deposition of collagen, resulting in scarring of the affected tissue(s).

Collagen Cross-linked by Allysine Shows a Different Molecular Packing in Fibrils and is More Easily Degraded Compared to Collagen Cross-linked by Hydroxyallysine The bone collagen in Bruck syndrome lacks the hydroxyallysine cross-links of normal bone; the cross-links are replaced by allysine cross-links [R. A. Bank et al., 1999, Proc. Natl. Acad. Sci. USA, 96: 1054–1058]. To corroborate whether allysine cross-linked collagen molecules are more prone to degradation by proteolytic enzymes, both demineralized Bruck syndrome bone (containing allysine cross-links) and demineralized control bone (containing hydroxyallysine cross-links) were treated with pepsin dissolved in 0.5 M acetic acid. Demineralized Bruck syndrome bone treated with pepsin resulted in a release of 65% of the collagen molecules (compared to 5% of normal bone). Treatment of demineralized Bruck syndrome bone as well as demineralized control bone in 0.5 M acetic resulted in the solubilization of 7% and 1% of the collagen molecules, respectively, indicating that the value of 65% released collagen is mainly due to the action of pepsin.

Additional evidence that allysine cross-linked collagen molecules are more prone to degradation by proteolytic enzymes was obtained by measuring hydroxyproline (Hyp) levels in urine of Bruck syndrome patients. We analyzed the urine of patients clinically diagnosed with Bruck syndrome (most patients have been described in the literature). The data presented in one of the examples show that the urinary level of hydroxyproline (μmol Hyp/mmol creatinine) in Bruck syndrome is higher than age-related controls or age-related osteogenesis imperfecta patients (FIG. 1A; $P<0.001$), showing that there is an increase of collagen degradation. The same can be concluded from the elevated hydroxyproline/proline ratio (FIG. 1B; $P<0.001$). As most of the collagen degradation products in urine are derived from bone [M. S. Calvo et al., 1996, Endocrine Reviews, 14: 333–368], it is likely that Bruck syndrome patients show an increased turnover of bone collagen. Indeed, Bruck syndrome patients are osteoporotic, which is a further indication of increased bone collagen degradation. This phenomenon is attributable to the lack of hydroxyallysine cross-links in Bruck syndrome bone.

Interestingly, pepsinized collagen from Bruck syndrome bone (containing predominantly allysine cross-links) shows on SDS-electrophoresis two β-bands (β1,1 and β1,2 in a 1:2 ratio) whereas pepsinized collagen from normal bone (containing predominantly hydroxyallysine cross-links) shows on SDS-electrophoresis three β-bands (β1,1, β1,2 and β2,2 in a 1:1:1 ratio). The β-bands are two α-chains connected to one another by means of a di-functional cross-link. Cross-linking of collagen involves a few specific amino acids only. For steric and chemical reasons only these amino acids are able to react with each other when collagen molecules are correctly aligned. Consequently, variations in the packing arrangement must have an impact on the amount and nature of cross-links, or vice versa. In either case, cross-link patterns can be used as a marker to probe the alignment of intrafibrillar collagen molecules. It occurs to us that the difference in β-band patterns after pepsinization is the result of a different packing of the collagen molecules. J. Brinckmann et al. [1996, J. Invest. Dermatol., 107: 589–592] also disclosed that collagen molecules cross-linked by allysine show a packing arrangement within fibrils that is different from the packing of collagen molecules containing hydroxyallysine cross-links. We postulate that this difference in packing is causally involved in the observed increased degradation rate of allysine cross-linked collagen.

One of the examples describes a method for the preparation of collagenous compositions showing various ratios of hydroxyallysine over allysine cross-link ratios, thus showing various degradation rates towards proteinases.

In conclusion, collagen molecules cross-linked by allysine are both in vitro and in vivo more prone to proteolytic degradation. This explains the high excretion of collagen degradation products in urine of Bruck syndrome patients and consequently the osteoporotic status of the patients. Vice versa, one can state that collagen cross-linked by hydroxyallysine is more resistant towards proteinases. This observation provides new tools for the preparation of collagenous materials exhibiting various degradation times in environments containing one or more proteinases: the residence time of collagenous materials can be increased by increasing the hydroxylysine level in the telopeptides. It is remarkable, that the effects of the type of enzymatically mediated cross-links on the susceptibility of collagen to proteolytic enzymes has never been investigated and never been taken into consideration as a tool for increasing or decreasing the biodegradation time of collagenous matrices, despite the fact that it is known for a long time that the presence of hydroxyallysine-derived cross-links is indicative for irreversible collagen deposition (such as is seen in fibrosis, see below). A possible explanation for this ignorance is, that it was untill now not known how the conversion of lysine into hydroxylysine of telopeptides could be controlled. The conversion is mediated by the enzyme telopeptide lysyl hydroxylase. In order to control the conversion of lysine into hydroxylysine of the telopeptides, one needs to know the identity of said enzyme and its working mechanism. We will show in the following paragraph (6.2) that the gene PLOD2 encodes for telopeptide lysyl hydroxylase.

Sequencing of PLOD2 in Bruck Syndrome Patients Revealed Mutations, Providing Direct Evidence that the Gene PLOD2 Encodes for Telopeptide Lysyl Hydroxylase Hydroxylation of Lys in the triple helix of collagen occurs exclusively on Lys present in the sequence Gly-X-Lys-Gly; a Lys in the X position is not hydroxylated. The hydroxylated Lys in the telopeptides is embedded in an entirely different amino acid sequence. In view thereof, the existence of two classes of enzymes has been postulated: a class of enzymes that converts the Lys in the triple helical sequence into hydroxylysine (Hyl) (helical lysyl hydroxylase) and a class of enzymes that is responsible for the conversion of Lys in the telopeptides into Hyl (telopeptide lysyl hydroxylase).

The most direct evidence that a class of telopeptide lysyl hydroxylases must exist has been derived from cross-link studies in Ehlers-Danlos type VI syndrome (EDS-VI) and Bruck syndrome. EDS-VI is a disease that is biochemically characterized by a hydroxylysine deficiency of the triple helix of collagen. EDS-VI patients show a normal level of pyridinolines in tissues (e.g. in collagen type I from bone) and a normal excretion level of pyridinolines in urine [B. Steinmann et al., 1995, Am. J. Hum. Genet., 57: 1505–1508; Açgil Y, et al., 1995, J. Am. Acad. Dermatol., 33: 522–524].

Pyridinolines are cross-links derived from the hydroxyallysine route. Thus, in EDS-VI, despite the deficiency of Hyl in the triple helix, a normal amount of Hyl is present in the telopeptides. From this it follows, that the mutated gene in EDS-VI is coding for a helical lysyl hydroxylase. In Bruck syndrome, the opposite is seen: in bone, normal Hyl levels of the triple helix of collagen is seen, whereas hydroxyallysine-derived cross-links are virtually absent [R. A. Bank et al., 1999, Proc. Natl. Acad. Sci. USA, 96:1054–1058]. Thus, in Bruck syndrome, despite normal levels of triple helical Hyl, a deficiency of Hyl in the telopeptides is observed. By definition, the mutated gene in Bruck syndrome is a telopeptide lysyl hydroxylase or a cofactor that is involved in TLH activity or a transcription factor that is involved in the expression/synthesis of the enzyme.

So far, three lysyl hydroxylase genes have been identified: PLOD1, PLOD2 and PLOD3. The abbreviation PLOD is derived from procollagen-lysine, 2-oxoglutarate 5-dioxygenase (which is the systematic name of lysyl hydroxylase), whereas the 1, 2 and 3 indicates the sequence of discovery. Expression of the three PLOD genes shows a tissue-specific distribution [M. Valtavaara et al., 1997, J. Biol. Chem., 272: 6831–6834; M. Valtavaara et al., 1998, J. Biol. Chem., 273: 12881–12886; K. Passoja et al., 1998, Proc. Natl. Acad. Sci. USA, 95: 10482–10486; H. Ruotsalainen et al., 1999, Matrix Biol., 18: 325–329]. PLOD2 also shows a tissue-specific splice variant [H. N. Yeowell & L. C. Walker, 1999, Matrix Biol., 18: 179–187]. Furthermore, there is some evidence at the DNA level that tissue-specific forms of PLOD1 exist [H. N. Yeowell et al., 1994, J. Invest. Dermatol., 102: 382–384]. PLOD1–3 have been expressed in a *Baculovirus* expression system; the proteins encoded by the cDNA exhibit activity towards the synthetic peptide containing the helical sequence IKGIKGIKG or ARGIKGIRGFSG. Although the specificity of the expressed gene products of PLOD1–3 towards the different collagen types has so far not been investigated, the relatively low amino acid sequence homology between the different lysyl hydroxylases (around 50–60%) suggests differences in the substrate properties or functionality of said enzymes.

PLOD1 is the gene that is mutated in Ehlers-Danlos type VI syndrome (EDS-VI) [J. Brinckmann et al., 1998, Arch. Dermatol. Res., 290: 181–186; H. N. Yeowell & L. C. Walker, 2000, Molec. Genet. Metab., 71: 212–224], a disease that is biochemically characterized by a hydroxylysine deficiency of the triple helix of collagen. In EDS-VI, a normal hydroxylation of the telopeptides is seen. Thus, the PLOD1 gene encodes most likely for a triple helical lysyl hydroxylase.

So far, no disease has been associated with PLOD2 or PLOD3. In a publication by R. A. Bank et al. [1999, Proc. Natl. Acad. Sci. USA, 96: 1054–1058], a Bruck syndrome family of Kurdish origin is shown where the defect (namely the absence of Hyl in the telopeptides of bone collagen) links to chromosome 17p12. This excludes PLOD2 and PLOD3 as candidate genes, as they are located on chromosome 3 and 7, respectively. The substrate specificity of the lysyl hydroxylase encoded by PLOD2 and PLOD3 is not known; the only substrate studies performed on both enzymes are incubations with a peptide displaying the helical sequence IKGIKGIKG or ARGIKGIRGFSG. Both enzymes were capable of hydroxylating these helical sequences [M. Valtavaara et al., 1997, J. Biol. Chem., 272: 6831–6834; M. Valtavaara et al., 1998, J. Biol. Chem., 273: 12881–12886; K. Passoja et al., 1998, Proc. Natl. Acad. Sci. USA, 95: 10482–10486]. From these data one would conclude that PLOD2 and PLOD3 encode for helical lysyl hydroxylases.

In addition, PLOD2 is expressed in skin [H. N. Yeowell & L. C. Walker, 1999, Matrix Biology, 18: 179–187; C. Wang et al., 2000, DNA and Cell Biology, 19: 71–77], a tissue where hydroxyallysine cross-links are present in extremely low levels. This would again suggest, that PLOD2 encodes for a helical lysyl hydroxylase.

Figure 7:
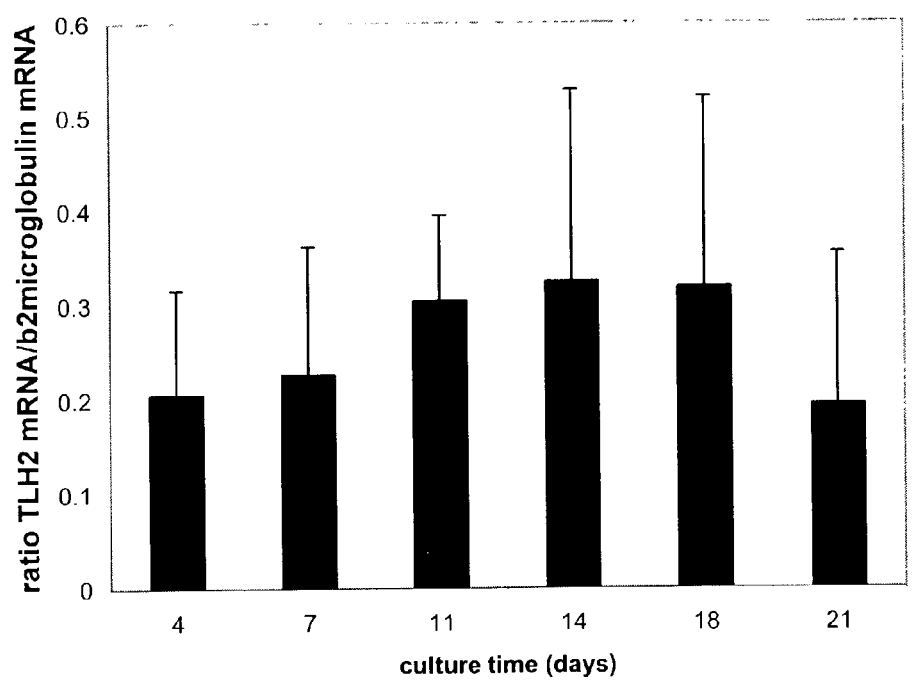
FIG. 7 is a graph showing the expression of PLOD2B during osteogenic differentiation of human bone marrow cells. The amount of mRNA derived from PLOD2B is essentially the same in the various differentiation phases.

A study on osteoblasts and/or precursors thereof provided data that the elevation of Lys hydroxylation in the telopeptides of type I collagen at day 16 (mineralization stage) coincide with a higher expression of PLOD2 mRNA [K. Uzawa et al., 1999, J. Bone Miner. Res., 14: 1272–1280]. Based on these data, the authors hypothesized that the PLOD2 gene might be involved in telopeptide lysyl hydroxylation. However, the data are not convincing: for the formation of pyridinoline cross-links a few days are required, and in this period PLOD2 expression is low, as is shown by said authors (their FIG. 3, second row, mRNA levels at the early differentiation stage=day 8). Their conclusion has therefore subsequently been ignored by other workers in the field. In fact, we have measured PLOD2 levels in asteoblasts and/or precursors thereof as well and did not find an increase of PLOD2 levels during osteoblastic differentiation, including the mineralization stage (FIG. 7). This was done with real-time PCR technology, which is much more reliable than the Northern blot technology used by Uzawa et al.

Figure 2:
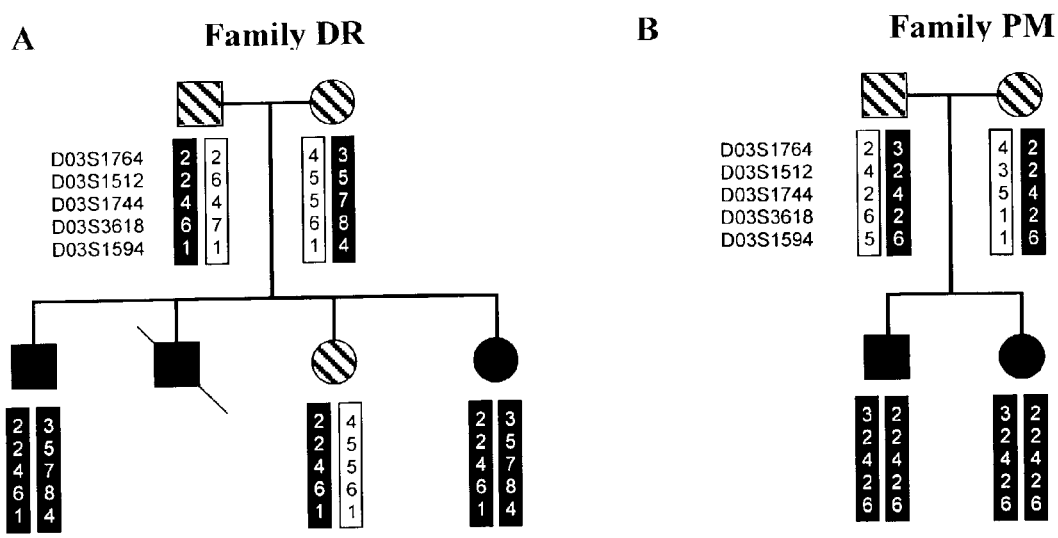
FIG. 2 is a pedigree of a Bruck syndrome family (family DR and family PM) showing the genotypes in the region of homozygosity on chromosome 3 reference interval D03S1764-D03S1594 (164.6–168.3 cM) where the gene PLOD2 is located. Black symbols denote affected individuals and striped symbols denote carriers of the disease. The haplotypes co-segregating with the disease are indicated with a black box. Both pedigrees provide evidence that PLOD2 is the candidate gene for telopeptide lysyl hydroxylase.

We have now investigated another consanguineous Bruck syndrome family (family PM) of Kurdish origin with 2 affected children but without healthy children (one of the children is case 8 of E. J. Breslau-Siderius et al., 1998, J. Pediatr. Orthop. B, 7: 35–38). In this pedigree an absence of linkage was found with our published markers of chromosome 17: haplotype analysis revealed that the affected children inherited different maternal chromosomes. The lysyl hydroxylase encoded by PLOD2 is, according to Gene Map 98, located on chromosome 3 between the interval D3S1550 and D3S1306 (sex average 159.8 cM and 164.25 cM, respectively). Haplotype analysis was carried out of the parents and the two affected with the DNA markers D03S1764 (sex average 152.62 cM), D03S1512 (sex average 158.38 cM), D03S1744 (161.04 cM), D03S3618 (163.18 cM and D03S1594 (168.94 cM). The affected individuals were homozygous for D03S1512, D03S1744, D03S3618 and D03S1594 and haplotype analysis showed that the affected children inherited two identical copies of that chromosomal region (i.e. homozygous by descent) (FIG. 2B). Thus, a good linkage was found in this Bruck syndrome family and the chromosomal region where PLOD2 is located. In conclusion, this Bruck syndrome family surprisingly provides genetic evidence that the lysyl hydroxylase encoded by PLOD2 is telopeptide lysyl hydroxylase. A second Bruck syndrome family (family DR) also shows linkage to chromosome 3 (FIG. 2A).

The primary structure of PLOD2 published in literature is primarily based on a cDNA sequence, meaning that the intron/exon boundaries are not known. PLOD1 and PLOD2 have 19 exons; intron/exon boundaries of these two genes are identical. As PLOD2 is highly homologous with PLOD1 and PLOD3, it is also expected that the exon/intron boundaries coincide with that of PLOD1 and PLOP3. This was confirmed by analyzing the sequence of Homo sapiens chromosome 3 clones RP11-758114 (GenBank code AC053539) and RP11274H2 (GenBank code AC018369). In addition, an extra exon (not seen in PLOD1 and PLOD3), designated as exon 13A, is an integral part of PLOD2. To provide direct evidence that PLOD2 encodes for a telopeptide lysyl hydroxylase, exon 1 to exon 19 as well as exon 13A were individually amplified by means of a polymerase chain reaction (PCR) with primers located in the introns flanked at the 5' and 3' side of each exon using TaKaRa La Taq polymerase. This was done with genomic DNA (purified by means of standard methods) from Bruck syndrome patients, from the unaffected parents, and from commercially available genomic DNA obtained from a healthy control population (Roche Diagnostics, Cat.No. 1691112). Amplified exons of the expected size (as determined on 1% agarose gels) were separated from the free dNTP's and the polymerase by means of the Qiagen PCR purification kit. The purified exons were stained with fluorescent labeled dideoxy nucleotides (ddNTP's) in a cycle sequence PCR using the ABI PRISM™ BigDyc Termination Cycle Sequencing Ready Reaction Kit and analyzed by means of capillary electrophoresis using the ABI PRISM™ 310 apparatus. For details of the used primers and PCR conditions for the amplification of the individual exons see one of the Examples. Sequence analysis of two Bruck syndrome patients of family PM revealed a nucleotide missense mutation resulting in a Gly6→Val mutation in the sequence GGYENVPT (SEQ ID NO: 1). This mutation was found on both alleles. Both parents were carrier for this missense mutation (see FIG. 3). In one Bruck syndrome patient of family DR a nucleotide missense mutation resulting in a Tbr→Ile mutation in the sequence GGYENVPT (SEQ ID NO: 1). The patient was homozygous for the mutation while both parents and a healthy sister were heterozygous for this mutation (see FIG. 4). The two different point mutations found in family PM and DR were situated in a sequence that shows 100% amino acid homology between the different PLOD2 and between different species. This suggests an important role of this region in the function of lysyl hydroxylases in general and that of PLOD2 in particular.

In conclusion, we have shown in this paragraph, much to our surprise in view of the evidence that pointed in another direction, that PLOD2 encodes for a telopeptidyl lysyl hydroxylase. This satisfies a need in the art by providing a new tool in the preparation of collagenous compositions showing various resistance times towards proteinases as it is now possible to regulate the hydroxylysine levels in the telopeptides.

Methods for Increasing or Decreasing Hydroxyallysine Cross-links Over Allysine Cross-links by Means of Modulating Telopeptide Lysyl Hydroxylase Expression The invention provides a method of treating a fibrotic condition in a mammal by administering to said mammal an effective amount of a compound or composition which reduces the lysyl hydroxylation level of collagen telopeptides and thereby results in a collagenous matrix having a decreased ratio of hydroxyallysine cross-links to allysine cross-links. As to the exact method of administration, dose to be administered and treatment protocol, the invention is not particularly restricted. These factors depend much on factors such as the active substance or composition to be administered, the tissue to be treated, the patient to be treated, the extent of the fibrosis, etc. For example, topical or subcutanous administration would be administration routes of choice when fibrosis occurs in skin or other easily accessible tissues. Administration by inhalation would be a preferable route of administration with fibrosis in lung tissue. Systemic administration, e.g. by intravenous injection or infusion, may be necessary when the fibrosis occurs in internal tissues, such as liver. The active agent may be coupled to a means for targeting to a particular site or tissue. The skilled person may determine for each individual case the best treatment strategy, with respect to route of administration, active substance or composition to be administered and dose and treatment protocol.

An approach to inhibit the conversion of telopeptide lysine into hydroxylysine for the preparation of collagenous materials with decreased hydroxylysine levels is the inhibition of transcription of the responsible telopeptide lysyl hydroxylase gene. A compound capable of silencing the promotor region of telopeptide lysyl hydroxylase is a potentially attractive compound for modifying the amount of hydroxyallysine cross-links over allysine cross-links. Compounds worthwhile to investigate are for example minoxidil and minoxidil analogues, compounds known to inhibit the transcription of the PLOD1 gene [S. Murad et al., 1994, Arch. Biochem. Biophys., 308: 42–47].

A further approach to inhibit the synthesis of telopeptide lysyl hydroxylase is the inhibition of mRNA translation by means of antisense RNA (the transcription product of the DNA antisense strand, i.e. the strand that does not encode a protein). Transfection of the cells can be done with naked antisense RNA, antisense RNA emulsified in or coupled to carriers or vectors containing (parts of) the PLOD2 DNA antisense strand.

Another approach to inhibit the conversion of telopeptidyl Lys into Hyl is inhibition of the activity of the enzyme telopeptide lysyl hydroxylase itself. Prolyl hydroxylase and lysyl hydroxylase have very similar catalytic properties (e.g. they share the same co-substrates). In addition, the inhibition patterns of prolyl and lysyl hydroxylases are very similar as well, but differences exists in some details, suggesting that significant differences exist between the catalytic sites of said hydroxylases. For example, $K_I$ values of the aliphatic and aromatic 2-oxoglutarate analogues (see below) are distinctively higher for lysyl hydroxylase encoded by PLOD1 than for prolyl 3-hydroxylase and prolyl 4-hydroxylase. The data that have previously been obtained with respect to the inhibition of prolyl 3-hydroxylase, prolyl 4-hydroxylase and helical lysyl hydroxylase encoded by PLOD1 can be used for a knowledge-based design of inhibitors of telopeptide lysyl hydroxylase. The assumption is strengthened by the observation, that the hydroxylation reaction carried out by the enzyme encoded by PLOD2 can be followed, like that of PLOD1, by measuring the decarboxylation of 2-oxo-[1-$^{14}$C] glutarate [Valtavaara et al., 1997, J. Biol. Chem., 272: 6831–6834].

The comparable reaction mechanism of the enzyme encoded by PLOD2 with that of the enzyme encoded by PLOD1 provides a window with respect to the design of telopeptide lysyl hydroxylase inhibitors for those skilled in the art. What follows is a description of the reaction mechanism of the protein encoded by PLOD2 based on previous findings for the protein encoded by PLOD1, followed by descriptions how this reaction mechanism can be inhibited. This should provide the skilled artisan sufficient guidance as the techniques closely parrallel experiments described in the past with respect to inhibition of the enzyme encoded by PLOD1. Lysyl hydroxylase acts on lysine in a reaction that requires ferrous ion ($Fe^{2+}$), 2-oxoglutarate, molecular oxygen ($O_2$) and ascorbate. The 2-oxoglutarate is stoichiometrically decarboxylated during hydroxylation with one atom of the $O_2$ being incorporated into succinate while the other is complexed to the enzyme-bound ferrous ion. The latter results in a highly reactive iron-oxygen complex, ferryl ion. The oxygen atom of the ferryl ion is subsequently incorporated into the hydroxy group formed on the lysine residue, thereby converting the ferryl ion to the enzyme-bound ferrous ion. In the absence of a hydroxylatable substrate, lysyl hydroxylase is able to catalyze the decarboxylation reaction of 2-oxoglutarate in the presence of all the co-substrates [G. Tschank et al., 1994, Biochem. J., 300: 75–79]. In this so-called uncoupled reaction, the ferryl ion is converted to $Fe^{3+}$ and OH, and the $Fe^{3+}$ ion remains bound to the active site, making the enzyme unavailable for new catalytic cycles until the $Fe^{3+}$ is reduced into $Fe^{2+}$ by ascorbate. The main role of ascorbate in the lysyl hydroxylase reaction in vivo is that of reactivating the enzyme after an uncoupled reaction [R. Myllylä et al., 1984, J. Biol. Chem., 259: 5403–5405]. As such, ascorbate plays a housekeeping role of restoring the iron constituent of the enzyme to the reduced state should it become oxidized adventitiously. The uncoupled reaction (and thus the oxidation of the iron) can be enhanced by peptides containing an unhydroxylatable sequence [D. F. Counts et al., 1978, Proc. Natl. Acad. Sci. USA, 75: 2145–2149; N. V. Rao & E. Adams, 1978, J. Biol. Chem., 253: 6327–6330].

The enzymatic reaction that converts telopeptide lysine into hydroxylysine can be used for the design of compounds that inhibit the activity of telopeptide lysyl hydroxylase without inhibiting lysyl oxidase. Examples of such potential inhibitors are:

Compounds (such as aliphatic and aromatic structural analogues of 2-oxoglutarate) that bind to the subsite(s) of active site of the enzyme destined for the binding of 2-oxoglutarate. The inhibition of telopeptide lysyl hydroxylase activity by said compounds is competitive with respect to 2-oxoglutarate.

Compounds that chelate $Fe^{2+}$ bound in the active site of telopeptide lysyl hydroxylase. The inhibition of telopeptide lysyl hydroxylase activity by said compounds is competitive with respect to the oxygen atom acceptor function of $Fe^{2+}$ and/or with respect to the binding of $Fe^{2+}$ to 2-oxoglutarate.

Syncatalytic inactivation of telopeptide lysyl hydroxylase by anthracyclines or coumalic acid analogues.

Syncatalytic inactivation of telopeptide lysyl hydroxylases by peptides containing an unphysiologic lysine derivate in a hydroxylatable position.

Hydroxylatable peptides or peptidomimetics that are competitive with respect to the natural substrate (telopeptides) of telopeptide lysyl hydroxylase. A selective peptide or peptido mimetic is much less competitive with respect to the natural substrate of lysyl oxidase.

Non-hydroxylatable peptides or peptido mimetics that are competitive with respect to the natural substrate (telopeptides) of telopeptide lysyl hydroxylase. A selective peptide or peptido mimetic is much less competitive with respect to the natural substrate of lysyl oxidase.

Compounds that compete with collagen for the peptide substrate binding site on telopeptide lysyl hydroxylase. Possible examples are the organophosphate-like compounds like malathion and its oxidized derivative malaoxon, shown to inhibit helical lysyl hydroxylase [A. Samimi & J. A. Last, 2001, Toxicol. Appl. Pharmacol., 176: 181–186].

The uncoupled reaction of lysyl hydroxylase can be used for the design of compounds that inhibit the activity of telopeptide lysyl hydroxylase. Potent compounds are:

Non-reducing ascorbate analogues that bind to the enzyme's active site but are not able to act as a specific alternative acceptor of ferryl oxygen. The presence of such a compound in the active site instead of an ascorbate (or an ascorbate analogue capable of reducing the ferryl ion) results in the inactivation of the enzyme by self-oxidation. The inhibition of telopeptide lysyl hydroxylase activity by said non-reducing ascorbate analogues is competitive with respect to ascorbate.

Peptides or peptido mimetics with an unhydroxylatable sequence, capable of enhancing the uncoupled reaction of telopeptide lysyl hydroxylase. Said inhibitors result in increased levels of self-oxidized (non-active) levels of telopeptide lysyl hydroxylase.

A large number of studies have been published with respect to the inhibition of prolyl hydroxylase and helical lysyl hydroxylase by means of peptides or other compounds. What follows are a few selected examples of studies that can be used as a starting point in the design of inhibitors for telopeptide lysyl hydroxylase without affecting lysyl oxidase. Examples of syncatalytic inactivation by peptides: V. Günzler et al., 1988, J. Biol. Chem., 263: 19498–19504; K. Karvonen et al., 1990, J. Biol. Chem., 265: 8145–8419. Examples of syncatalytic inactivation by coumalic acid and anthracyclines: V. Günzler et al., 1987, Biochem. J., 242: 163–169; V. Günzler et al., 1988, Biochem. J., 251: 365–372. Examples of inhibitory competitive analogues of 2-oxoglutarate and ascobate: K. Majamaa et al., 1984, Eur. J. Biochem., 138: 239–245; K. Majamaa et al., 1985, Biochem. J., 229: 127–133; K. Majamaa et al., 1986, J. Biol. Chem., 261: 7819–7823. Examples of conformational requirements of lysyl hydroxylatable peptides: P. Jiang & V. S. Ananthanarayanan, 1991, J. Biol. Chem., 266: 22960–22967.

Apart from the knowledge-based design of inhibitors of telopeptide lysyl hydroxylase, a search can be performed with a library of compounds in order to find a compound that inhibitis the activity of telopeptide lysyl hydroxylase, but not lysyl oxidase.

A further example of inhibition of the catalytic properties of telopeptide lysyl hydroxylase is the use of antibodies. Antibodies directed against the enzyme and capable of blocking the active site or inhibiting the hydroxylation by telopeptide lysyl hydroxylase otherwise are potent inhibitors of the enzymatic reaction. These antibodies, preferably monoclonal, can be generated by immunization of mice with synthetic peptides or peptidomimetics containing stretches of amino acids of telopeptide lysyl hydroxylase, in particular sequences around the residues responsible for the binding of $Fe^{2+}$ or 2-oxoglutarate to the enzyme. Promising candidate peptides or peptidomimetics for the generation of inhibiting antibodies are likely (but not necessarily) to be derived from the last 60 residues at the carboxy-terminal end of the enzyme (i.e. the region containing the conserved residues known to play a role in the catalytic properties of lysyl hydroxylase encoded by PLOD1). Monoclonal antibodies can also be generated by screening phage display libraries in their ability to block the activity of telopeptide lysyl hydroxylase. Antibodies not directed to the active site but directed against parts of the enzyme that are important for substrate binding are also potent inhibitors of the enzymatic reaction. In addition, antibodies directed towards the collagen telopeptides are also expected to inhibit the hydroxylation reaction of telopeptide lysyl hydroxylase by means of steric hindrance. Besides monoclonal or polyclonal antibodies, intracellular antibodies (intrabodies) can be used. Such intrabodies are encoded by engineered genes that are expressed within the cells of interest [I. J. Rondon & W. A. Marasco, 1997, Annu. Rev. Microbiol., 51: 257–283].

Alternatively, aptamers can be used to inhibit the reaction catalyzed by telopeptide lysyl hydroxylase. Aptamers are selected nucleic-acid binding species that bind to a target molecule with high affinity and specificity (the Latin word "aptus" means "to fit"). Nucleic acid aptamers that bind to telopeptide lysyl hydroxylase can be readily selected by the SELEX process, a technique for screening very large combinatorial libraries of oligonucleotides by an iterative process of in vitro selection and amplification [S. D. Jayasena, 1999, Clin. Chem., 45: 1628–1650]. The library typically contains $10^{14}$–$10^{15}$ random DNA sequences flanked by two fixed sequence regions. Sequences that bind to the target molecule (the latter being fixed on a solid support) are separated from sequences that do not bind by a simple washing step. The population of sequences bound to the target is amplified by PCR using primers to the two fixed sequence regions. The enriched library can be used for the next selection/amplification cycle. The enrichment efficieny of high-affinity binders is governed by the stringency of selection at each round. The enriched library is cloned and sequenced to obtain the sequence information of each member. The generated aptamers have to be screened for their ability to inhibit the target enzyme by means of an assay designed to measure the activity of telopeptide lysyl hydroxylase.

In yet another approach to inhibit the conversion of telopeptide lysine into hydroxylysine is the delivery of constructs containing a telopeptide lysyl hydroxylase that is able to bind telopeptides but is not capable to convert the lysine of the telopeptides into hydroxylysine. Such an exogenous telopeptide lysyl hydroxylase is competitive to endogenous telopeptide lysyl hydroxylase with respect to its natural substrate (telopeptides). For said construct telopeptide lysyl hydroxylase can be used that is mutated by means of site-directed mutagenesis. Candidate residues for site-directed mutagenesis are the mutated residues found in Bruck syndrome. Other candidate residues for site-directed mutagenesis are the residues that are needed for the full activity of helical lysyl hydroxylase [A. Pirskanen et al., 1996, J. Biol. Chem., 271: 9398–9402] and that are conserved in the lysyl hydroxylase encoded by PLOD2. Especially interesting are the three ligands needed for the binding of $Fe^{2+}$ to the catalytic site of lysyl hydroxylase (for helical lysyl hydroxylase encoded by PLOD1 this is His-638, Asp-640 and His-690; numbering begins with the first residue in the processed polypeptide) or the residue that is responsible for the binding of 2-oxoglutarate to the enzyme (which is Arg-700 for the helical lysyl hydroxylase encoded by PLOD1) [K. Passoja et al., 1998, FEBS Letters, 434: 145–148]. The same residues are conserved in PLOD2. Residues that are also of potential interest are glycosylated Asn-X-Thr/Ser sequences: glycosylated lysyl hydroxylase encoded by PLOD1 has a higher activity than its deglycosylated counterpart [R. Myllylä et al., 1988, Biochem. J., 253: 489–496]. It thus seems that asparagine-linked oligosaccharides are required to obtain maximum lysyl hydroxylase activity. Two potential attachment sites for asparagine-linked oligosaccharides of the lysyl hydroxylase encoded by PLOD2 have an homologous location in the sequence of the helical lysyl hydroxylase encoded by PLOD1. Other residues of potential interest are the cysteines of lysyl hydroxylase 2. These examples should not be construed as limiting.

A further embodiment of the subject invention for inhibiting the conversion of telopeptide lysine into hydroxylysine is the administration of an effective quantity of peptides comprising a hydroxylatable Lys. Peptides which act as enzyme substrates reduce the levels of enzyme available for hydroxylating collagen telopeptides. A method for the delivery of such peptides into the cells is the delivery of plasmid constructs containing the nucleotide sequence encoding for such peptides.

Pathological Levels of Hydroxallysine Cross-links Results in an Unwanted Accumulation of Collagen Molecules (Fibrosis)

In abnormal wound healing of the skin, such as in hypertrophic scarring, large amounts of hydroxyallysine-derived cross-links (such as DHLNL) are seen [A. J. Bailey & N. D. Light, 1985, Ciba Found. Symp., 114: 80–96]. A predominance of DHLNL is also found in collagen produced after wounding of the corneal stroma; the resulting scar shows markedly increased levels of hydroxyallysine derived cross-links at the expense of allysine cross-links [D. J. Cannon & S. Cintron, 1975, Biochim. Biophys. Acta, 412: 18–25]. The pioneering studies on elevated hydroxyallysine-derived cross-links in abnormal scarring were later confirmed, followed by reports on increased hydroxyallysine-derived cross-links in other (mainly fibrotic) disorders, such as various lung diseases (respiratory distress syndrome, idiopathic pulmonary fibrosis, hypersensitivity pneumonitis, respiratory bronchiolitis, silicosis and bleomycin-induced lung fibrosis), chronic adriamycin nephropathy (an experimental model resulting in non-immunologic glomerulosclerosis and interstitial fibrosis), infarct scar of the myocardium, joint contractures, vessel luminal narrowing, lipodermatosclerosis, annulo-aortic ectasia, fibrotic lesions of Dupuytren's disease, skin of patients with lipoid proteinosis, diabetes, skin fibrosis due to chromoblastomycosis infection, skeletal muscle injury, tendon hypertrophy and various liver diseases such as in alveolar echinococcosis (a dense and irreversible fibrosis), hepatocellular carcinoma, alcoholic cirrhosis or cirrhotic livers induced by viral hepatitis or by Schistosoma mansoni. From this abundant amount of data on elevated hydroxyallysine cross-link levels in fibrotic tissues we can conclude that one of the characteristics of fibrotic lesions is an upregulation of telopeptide lysyl hydroxylase.

In recent years, it has been suggested that the relative (and absolute) amount of hydroxyallysine cross-links are adequate biomarkers for the accumulation of collagen in lung and liver fibrosis [J. A. Last et al., 1990, Am. Rev. Respir. Dis., 141: 307–313; S. Ricard-Blum et al., 1995, Parasite, 2: 113–118]. As the same is seen in other fibrotic tissues (such as skin and kidney), it was actually stated that "It is possible that organ fibrosis is a unique process ultimately associated with a change in cross-linking whereby the proportion of the allysine cross-links decreases in favor of the hydroxyallysine-derived cross-links" [J. Brinckmann et al., 1996, J. Invest. Dermatol., 107: 589–592]. Thus, hydroxyallysine cross-links are implicated in the pathogenesis of fibrosis. As a matter of fact, hydroxyallysine cross-link levels might be an important criterion in assessing the irreversibility of fibrosis. The validity of this statement is strengthened by cross-link patterns seen in acute (self-limiting) and progressive forms of fibrosis. Collagen produced in response to an injury of skin is initially stabilized by DHLNL, a cross-link derived from hydroxyallysine. In the early stages of wound healing, the collagen of both forms of fibrosis possess DHLNL as the major cross-link, but after a few months there is an approximately equal proportion of HLNL. Subsequently, acute and progressive fibrosis follow a different course. In hypertrophic scars, a progressive form of skin fibrosis, the 1:1 ratio of the two cross-links is retained. In contrast, the cross-link pattern in the self-limiting form of fibrosis gradually reverts to normal, i.e.

there is a disappearance of hydroxyallysine derived cross-links and replacement by allysine derived cross-links. In addition, the HLNL of old hypertrophic scars is derived from hydroxyallysine, and therefore stabilized by undergoing the Amadori rearrangement. The HLNL of normal scars is like normal dermis in being almost entirely derived from allysine [A. J. Bailey & N. D. Light, 1985, Ciba Found. Symp., 114: 80–96].

The data mentioned in this paragraph provides additional evidence for our statements that collagen cross-linked by means of hydroxyallysine derived cross-links is more difficult to degrade than collagen cross-linked by means of allysine derived cross-links. The data indicate that the type of cross-links provides a mechanism for regulating the rate of collagen catabolism: collagen with hydroxyallysine cross-links is less susceptible to proteolytic degradation than collagen cross-linked by allysine residues. Clearly, the production of collagen containing telopeptide lysine instead of telopeptide hydroxylysine would be beneficial for treating fibrotic conditions. Inhibition of telopeptide lysyl hydroxylase (to enhance the formation of allysine cross-links at the expense of hydroxyallysine cross-links) is an attractive way for interfering with a fibrotic respons by reducing the amount of hydroxyallysine derived cross-links over allysine-derived cross-links, making the collagen more susceptible to proteolytic degradation. In the next paragraph we will show that PLOD2, encoding telopeptide lysyl hydroxylase, is indeed highly expressed in fibrotic cells.

Fibrotic Cells Contain High Levels of PLOD2 mRNA

Figure 5:
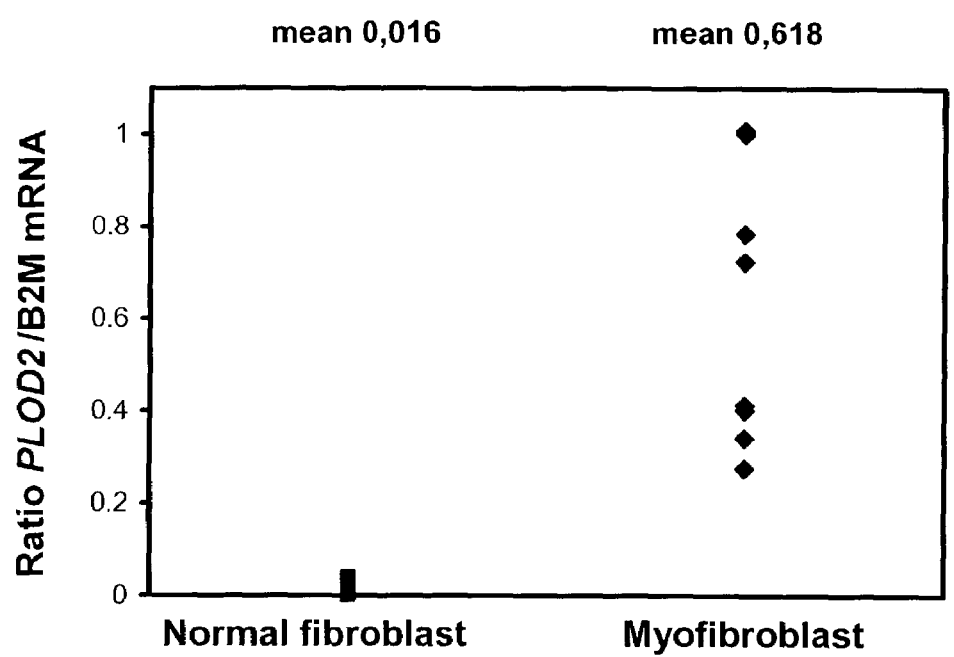
FIG. 5 is a graph showing the mRNA levels of PLOD2B (normalized against $\beta$2-microglobulin mRNA levels) in cultured human fibroblasts and cultured human myofibroblasts as determined by multiplex real-time PCR. The data show that PLOD2B is highly expressed in myofibroblasts, cells that play a key role in fibrotic processes.

Clearly, fibroblasts in fibrotic tissues (the so-called myofibroblasts) are fundamentally different from that of normal fibroblasts: myofibroblasts synthesize collagen with increased hydroxylysine levels of the telopeptides. Such collagen is destined to become irreversibly incorporated into the collagen network of the tissue by means of hydroxyallysine cross-links. The fact that HP, the maturation product of DHLNL, might serve as a permanent marker of a fibrotic event indicates that such cross-linked collagen molecules show a low to negligible rate of degradation. We have concluded in the previous paragraphs that hydroxylation of the telopeptide lysine is controlled by telopeptide lysyl hydroxylase, and that PLOD2 encodes for telopeptide lysyl hydroxylase. Therefore, PLOD2 must be overexpressed in myofibroblasts. We have checked this by measuring mRNA levels of PLOD2 in normal fibroblasts and in myofibroblasts by means of real-time PCR techniques. To strengthen our conclusion, that telopeptide lysyl hydroxylase is a key enzyme in fibrosis, we also measured mRNA levels of PLOD1, PLOD3, and collagen type I (COL1A1). FIG. 5 shows that myofibroblasts have in mean a 40-fold increase of PLOD2 mRNA levels compared to fibroblasts. In contrast, only a 4-fold increase was observed in PLOD1 and COL1A1 mRNA levels. PLOD3 levels were in most cases not elevated. The data indicate that telopeptide lysyl hydroxylase is highly upregulated in fibrotic tissues.

Measurement of PLOD2 mRNA, Teloptide Lysyl Hydroxylase Protein Level or Telopeptide Lysyl Hydroxylase Activity Level as a Tool to Diagnose or Monitor Fibrotic Processes The invention provides a method for diagnosing and/or monitoring the occurrence or state of a fibrotic process in a mammal comprising taking a sample from said mammal, analyzing said sample to determine the expression level of a PLOD2 gene and comparing said expression level with a standard. Suitable samples are tissue samples, in particular from tissues at risk for, or involved in, fibrotic processes. Suitable standards represent the expression level of a PLOD2 gene in normal tissues, i.e. not affected by fibrotic processes.

Detection of transcriptional acitivity of the gene PLOD2 may be achieved by assaying the level of mRNA derived from PLOD2 (e.g., by Northern blot analysis, mRNA analysis by competitive PCR or real time PCR), the protein level of telopeptide lysyl hydroxylase (e.g., by Western blot analysis, or by immunoassays such as ELISA), or the level of functional enzymatic activity of telopeptide lysyl hydroxylase (e.g., by means of hydroxylatable peptides).

In the first approach, transcriptional activity of the PLOD2 coding region can be assessed by hybridization assays. For example, RNA can be isolated and analyzed by Northern blot using a probe homologous to the telopeptide lysyl hydroxylase coding sequence or particular portions thereof. Estimation of mRNA levels can also be achieved by using PCR-based technologies, such as the conversion of mRNA to cDNA by reverse transcriptase, followed by e.g. competitive PCR or real-time PCR. A description of a real-time PCR to measure PLOD2 levels is given in one of the Examples.

In the second approach, the expression of the enzyme product (reflecting translational activity) can be assessed immunologically, for example by Western blots, immunoprecipitation, immunoassays such as enzyme-linked immunoassays and the like. The antibodies can be polyclonal, monoclonal, or chimeric of nature. The antibodies can be obtained by immunization of animals with the native or denatured enzyme or fragments thereof (such as synthetically manufactured peptides). Alternatively, the antibodies can be raised by means of the phage display method. The enzyme product can also be assessed by means of aptamers based on DNA/RNA sequences [S. D. Jayasena, 1999, Clin. Chem., 45: 1628–1650].

In the third approach, the expression of the enzyme product can be assessed by methods reflecting the enzymatic activity of the enzyme. Such methods are described in the next chapter.

High Through-put Assays for Measuring Telopeptide Lysyl Hydroxylase Activity

The invention provides an assay for screening compounds or compositions to determine their effect on telopeptide lysyl hydroxylase activity comprising contacting under enzymatically functional conditions a compound or composition to be tested with a PLOD2-encoded telopeptide lysyl hydroxylase enzyme and a suitable substrate for this enzyme, and determining the level of lysyl hydroxylation of the substrate compared to the level of lysyl hydroxylation of the substrate in the absence of the compound or composition to be tested.

The following description illustrates a method which can potentially lead to a high through-put assay for measuring the activity of telopeptidyl lysyl hydroxylase. Such an assay can be used for the screening of compounds in order to determine their antagonist properties, or as a tool to diagnose or monitor fibrotic processes.

A biotinylated peptide containing a telopeptide-like sequence containing at least one hydroxylatable Lys is subjected to incubation with telopeptide lysyl hydroxylase. The resulting mixture is treated with periodate or other suitable oxidizing agent. The 2-amino alcohol of Hyl in peptides has been shown to undergo rapid periodate oxidation to create an aldehyde [D. D. van Slyke et al., 1941, J. Biol. Chem., 141: 681–705]; the same occurs with peptides with a N-terminal Ser or N-terminal Thr. By designing a peptide substrate lacking N-terminal Ser or Thr in the peptide, only peptides containing a Hyl will form an aldehyde by means of periodate treatment. The aldehyde is then reacted with a tagging group, for instance in the form of a hydrazide, R'CONHNH$_2$ to form a hydrazone, R'CONHN═CH— peptide. R' can be any variety of useful groups, such as Lucifer Yellow, Texas Red or Cascade Blue. The biotinylated peptide can be separated from the remaining reaction mixture by immobilization based on the strong interaction of biotin with avidin or streptavidin. Other options are e.g. the use of peptides containing a repetitive His-sequence in combination with Ni$^{2+}$ carriers or SAMA-peptides in combination with maleimide carriers. Measuring the fluorescence of the tag attached to Hyl provides information about the conversion of the Lys of the peptide into Hyl by telopeptide lysyl hydroxylase. Tags can also be used that are suitable for calorimetric or radioactive measurements.

It should be stressed, that the oxidation of Hyl by periodate results in the stoichiometric release of formaldehyde. 4-Amino-3-pentene-2-one (fluoral P) is reported to selectively react with formaldehyde to form a fluorescent dihydropyridine product [H. Tsuchiya et al., 1994, Analyst, 119: 1413–1416], even when aldehyde concentrations 2000 times that of detectable formaldehyde are present. Thus, measuring the release of formaldehyde is another method to provide information whether the Lys of the peptide is converted into Hyl by telopeptide lysyl hydroxylase.

In yet another format, energy-transfer substrates can be prepared for measuring whether a Lys or a Hyl is present in the peptide. In this type of substrate, two chromophoric groups that form a Forster energy donor-acceptor pair are placed at opposite ends of a peptide. The fluorescence emission of the donor overlaps the absorption spectrum of the acceptor, causing the fluorescence of the donor to be quenched while the substrate remains intact. When the intervening peptide region is cleaved by a proteinase, relief of the strongly distance-dependent quenching provides the means to follow this activity. In concreto, a energy-transfer substrate (a peptide containing a telopeptide-like sequence containing at least one hydroxylatable Lys and containing a fluorophore and a quencher) is subjected to telopeptide lysyl hydroxylase followed by digestion with trypsin or lysyl endopeptidase. The latter cleaves the peptide bond at the C-terminal end of Lys; trypsin cleaves the peptide bond on the C-terminal side of Lys and Arg. Hydroxylation of Lys residues reduces their susceptibility to digestion by trypsin or lysyl endopeptidase [M. S. Molony et al., 1998, Anal. Biochem., 258: 136–137]. In this format, diminished increase of fluorescence is seen at a given time when the Lys is converted into Hyl.

Other high through-put formats may be based on antibodies or aptamers recognizing the non-hydroxylated peptide but not the hydroxylated peptide or vice versa.

EXAMPLES

Example 1

Pepsin Digestion of Normal and Bruck Syndrome Bone Shows Differences in Collagen Degradation by Proteolytic Enzymes and Differences in Collagen Packing Bruck syndrome and normal bone was demineralized at 4° C. with 0.5 M EDTA, 0.05 M Tris-HCI, pH 7.5 over 2 weeks. Demineralized Bruck syndrome and normal bone was incubated for 24 h at 4° C. with 0.5 M acetic acid (HAc) or with pepsin (enzyme:substrate ratio 1:10, w/w) in 0.5 M HAc. The solubilized collagen (present in the supernatant) was separated from the insoluble collagen matrix (containing the non-solubilized collagen) by means of centrifugation; both were hydrolyzed with 6 M HCI in Teflon sealed glass tubes (110° C., 20–24 h). The amount of the collagen-specific amino acid hydroxyproline (Hyp) was measured with reversed-phase high-performance liquid chromatography [R. A. Bank et al., 1997, Matrix Biol., 16: 233–243]. The amount of solubilized collagen was expressed as a percentage of total collagen using the equation $Hyp_{sup}/(Hyp_{res}+Hyp_{sup}) \times 100\%$ where $Hyp_{sup}$ is the amount of Hyp in the supernatant and $Hyp_{res}$ the amount of Hyp in the residual tissue.

Collagen solubility in 0.5 M acetic acid was 7% and 1% for Bruck syndrome and normal bone, respectively. Treatment with pepsin resulted in the release of 65% of the collagen from Bruck syndrome bone, whereas treatment with pepsin resulted in the release on only 5% of the collagen from normal bone. Clearly, the collagen molecules in the fibrils in Bruck syndrome bone are more prone to degradation by proteinases. As the triple helix of collagen type I in Bruck syndrome is normally modified, the increased release of collagen by pepsin of Bruck syndrome bone is due to the replacement of hydroxyallysine cross-links by allysine cross-links.

The pepsin-solubilized collagen of normal bone and Bruck syndrome bone was subjected to SDS-polyacrylamide gel electrophoresis and subsequently stained with Coomassie Brilliant Blue; the staining pattern of normal bone revealed three β-bands (β1,1, β1,2 and β2,2 in a 1:1:1 ratio) whereas the staining pattern of Bruck syndrome bone revealed two β-bands (β1,1 and β1,2 in a 1:2 ratio). The β-band patterns show that there are differences in the packing of intrafibrillar collagen molecules between normal and Bruck syndrome bone.

Example 2

Hydroxyproline Measurements in Urine Revealed That in Vivo Degradation of Bone Collagen is Enhanced in Bruck Syndrome Urine samples (500 µl) were hydrolyzed in an oven (110° C.; 20–24 h) with 500 µl 12 M HCI in 5 ml Teflon sealed glass tubes. After drying (SpeedVac, Savant), the hydrolysates were dissolved in 1 ml water, and diluted 400 times in 0.1 M borate buffer pH 9.5. A 200 µl sample was mixed with 25 µl o-phthaldialdehyde (OPA) reagent (30 mg OPA +15 µl β-mercaptoethanol in 1 ml acetone) and reacted for 1 min at room temperature. The reaction mixture was mixed with 25 µl iodoacetamide (80 mg/ml acetone) and incubated at room temperature for at least 30 sec to remove excess β-mercaptoethanol. Subsequently, the secondary amino acids hydroxyproline (Hyp) and proline (Pro) were derivatized with 50 µl 6 mM 9-fluorenylmethyl chloroformate in acetone for 5 min at room temperature. Immediately thereafter, the sample was extracted twice with 700 µl diethyl ether to terminate the reaction and to remove excess reagent. After the addition of 400 µl 25% (v/v) acetonitrile in 0.1 M borate buffer pH 8.0, a 50 µl aliquot of the derivatization mixture was injected into the HPLC system. In this way, 0.0208 μl of the original urine sample was applied onto the column. Reversed-phase chromatography of the samples on a Micropak ODS-80TM column (150 mm×4.6 mm; Varian, Sunnyvale, Calif., USA) was performed as described elsewhere [R. A. Bank et al., 1996, Anal. Biochem., 240: 167–176]; Hyp calibration was performed with an amino acid standard for collagen hydrolysates obtained from Sigma (A-9531; St. Louis, Mo., USA).

FIGS. 1A–B shows the urinary excretion of Hyp and the Hyp/Pro ratio in Bruck syndrome patients versus controls as a function of age. All patients show a high excretion of Hyp, indicating a high degradation rate of collagen. As most of the collagen degradation products in urine are derived from bone [M. S. Calvo et al., 1996, Endocrine Reviews, 14: 333–368], the data show that Bruck syndrome patients have an increased turnover of bone collagen. This is due to the replacement of hydroxyallysine cross-links by allysine cross-links in Bruck syndrome bone, making the collagen network more susceptible towards proteinases.

Example 3

Mutation Analysis of the PLOD2 Gene of Bruck Syndrome Patients Reveals that PLOD2 is Telopeptide Lysyl Hydroxylase Amplification of the individual exons of PLOD2 was carried out with the primers presented in table 1. The PCR mix consisted of 5 μl TaKaRa 10× PCR buffer, 8 μl of mixture containing the four dNTPs (2.5 mM each), 1 μl forward primer and 1 μl reverse primer (50 μM each), 0.5 μl TaKaRa La Taq polymerase (50 U/μl), 2.5 μl DNA (200 ng/μl), 5 μl DMSO and 27 μl H$_2$O. Thirtyfive cycles of amplification were carried out. Each cycle consisted of: 1 min denaturation at 94° C., 0.5–1.5 min at 56–60° C. for annealing (see table exact condition per primer set) and 1 min at 68° C. for the extension. The amplified exons were purified with the Qiagen PCR purification kit; 10 ng of each exon was subjected to a cycle sequence PCR using the ABI PRISM™ BigDye Termination Cycle Sequencing Ready Reaction Kit and analyzed by means of capillary electrophoresis using the ABI PRISM™ 310 apparatus.

TABLE 1

Primers used for the amplification of the individual exons of PLOD2

| Exon | Forward primer | Reverse primer | Product length | Annealing temperature |
|---|---|---|---|---|
| Promoter | 5' CTCCCAAAGCTAAGTGCAGG 3' (SEQ ID NO:4) | 5' AGACAGGGATTCCAGGGGT 3' (SEQ ID NO:23) | 524 bp | 56° C. 30" |
| 1 | 5' GTCTCTGCGTTCTCGCGAGA 3' (SEQ ID NO:5) | 5' AAGGGCTGTTGGATGAATGAAC 3' (SEQ ID NO:24) | 260 bp | 56° C. 1'30" |
| 2 | 5' TGAGGTCTCAATTACTGTAGTGA 3' (SEQ ID NO:6) | 5' CTTCCTTGTGAGGATTACAGATT 3' (SEQ ID NO:25) | 27.2 | 56° C. 1'30" |
| 3 | 5' GTACTGTTCAAGTTGATGATGTC 3' (SEQ ID NO:7) | 5' GCCACCGTGCCCAACCATATT 3' (SEQ ID NO:26) | 334 bp | 56° C. 30" |
| 4 | 5' ATGGTTTATGTGCCTAGATTCTGA 3' (SEQ ID NO:8) | 5' GGAACACCAACTCACATAATACA 3' (SEQ ID NO:27) | 390 bp | 56° C. 1'30" |
| 5 | 5' TTCTTTCATGGTGAGCTGTGA 3' (SEQ ID NO:9) | 5' TGATATCCAGCCAGGTGACA 3' (SEQ ID NO:28) | 442 bp | 56° C. 30" |
| 6 | 5' GCAACTATCGCAGTTTCTACCT 3' (SEQ ID NO:10) | 5' CCAAATGGACATAACAAAGGAAAG 3' (SEQ ID NO:29) | 331 bp | 56° C. 30" |
| 7 | 5' CACATACACACACAGACACACG 3' (SEQ ID NO:11) | 5' AAAGGCTATCACTCTGCTGAGG 3' (SEQ ID NO:30) | 379 bp | 64° C. 30" |
| 8 | 5' TAAAGGAATATACCTGCTGCAGA 3' (SEQ ID NO:12) | 5' ATTCCACTTACATCTACTGCAGA 3' (SEQ ID NO:31) | 234 bp | 56° C. 1'30" |
| 9 | 5' TTTCAAGTGTTAGAGAACTGCCA 3' (SEQ ID NO:13) | 5' CCACTGAACTTAACCCAATGAAT 3' (SEQ ID NO:32) | 392 bp | 56° C. 1'30" |
| 10 | 5' TCTAAGATTTCTAGGCTACAGGC 3' (SEQ ID NO:14) | 5' GTTGGCTACTGCATACGCAAAC 3' (SEQ ID NO:33) | 633 bp | 60° C. 30" |
| 11 | 5' CAGAAAAGTATGCTAGAGAACCA 3' (SEQ ID NO:15) | 5' GTAGAACATAACTAAGTTCCCTC 3' (SEQ ID NO:34) | 336 bp | 56° C. 1'30" |
| 12 | 5' CAGGTTTGTTGAATGAGCTTTCT 3' (SEQ ID NO:16) | 5' AGGATTCCAAGTGGTCTTGGG 3' (SEQ ID NO:35) | 398 bp | 60° C. 1'30" |
| 13 | 5' GGGGCAGTGGTTTATCTCCTA 3' (SEQ ID NO:17) | 5' CACAGTGACACACCAACTGGT 3' (SEQ ID NO:36) | 421 bp | 60° C. 1'30" |
| 13A | 5' AGAATACCTGAGAGAGCGGGT 3' (SEQ ID NO:18) | 5' ACGCAAACACACAGATGACTGA 3' (SEQ ID NO:37) | 265 bp | 60° C. 1'30" |
| 14 | 5' CAGTTGAGTGTCAGTGCTATCT 3' (SEQ ID NO:19) | 5' CTGGTGTGAGACAGTATCTCAT 3' (SEQ ID NO:38) | 492 bp | 60° C. 1'30" |
| 15 | 5' ATAAGCATATTCAGAACCAGGCA 3' (SEQ ID NO:20) | 5' CTCCACTTTCACATCTTCTGTG 3' (SEQ ID NO:39) | 340 bp | 60° C. 1'30" |
| 16 | 5' TCATCAATTCTGAGGTGCACCA 3' (SEQ ID NO:21) | 5' AGAAACCCGCCCAAACTAAT 3' (SEQ ID NO:40) | 501 bp | 56° C. 30" |
| 17 | 5' AGCAGATGATATACCACATTGGA 3' (SEQ ID NO:22) | 5' GTTCATGCCAGTCATTCATCCA 3' (SEQ ID NO:41) | 896 bp | 60° C. 30" |
| 18 | 5' AGCAGATGATATACCACATTGGA 3'* (SEQ ID NO:22) | 5' GTTCATGCCAGTCATTCATCCA 3' (SEQ ID NO:41) | 896 bp | 60° C. 30" |
| 19 | 5' AGCAGATGATATACCACATTGGA 3'* (SEQ ID NO:22) | 5' GTTCATGCCAGTCATTCATCCA 3' (SEQ ID NO:41) | 896 bp | 60° C. 30" |

Primers used for sequencing are shown in bold.
*Sequence primer for exon 18 is 5' GGTCTTTGCAGGCTATTATA 3' and for exon 19 is 5' GCTCAAATGACATAATTTG (SEQ ID NO:42)

Sequence analysis of two Bruck syndrome patients of family PM, showed a G→T nucleotide missense mutation resulting in a Gly→Val amino acid substitution in the sequence GGYENVPT (SEQ ID NO: 1) (the mutated Gly is underligned). This mutation was found on both alleles. Both parents were carrier of this missense mutation (see FIG. 3). In one Bruck syndrome patient of family DR a C5T nucleotide missense mutation is seen resulting in a Thr→Ile amino acid substitution in the sequence GGYENVPT (SEQ ID NO: 1). The patient was homozygous for the mutation while both parents and a healthy sister were heterozygous for this mutation (see FIG. 4). The two different point mutations found in family PM and DR were situated in a sequence that shows 100% homology between the different PLODs and between different species. This suggests an important role of this region in the function of lysyl hydroxylases in general and that of PLOD2 in particular. Bruck syndrome is characterized by defective telopeptide lysyl hydroxylase activity [R. A. Bank et al., 1999, Proc. Natl. Acad. Sci. USA, 96: 1054–1058]. The above described mutations show that PLOD2 encodes telopeptide lysyl hydroxylase.

The knowledge that PLOD2 encodes for telopeptide lysyl hydroxylase provides the skilled artisan the necessary information for increasing or decreasing the hydroxylysine levels in the telopeptides of collagen by increasing or decreasing the enzyme activity level of telopeptide lysyl hydroxylase in cells during collagen synthesis. The synthesized collagen can subsequently be harvested by standard purification methods for the preparation of collagenous materials (such as collagen matrices as supports for new tissue growth, or collagen-based wound dressings) with increased or decreased turnover times.

Example 4

Preparation of Collagenous Matrices with Increased or Decreased Turnover Times

A number of methods has been disclosed to isolate collagen from tissues. This collagen can subsequently be used for the preparation of collagen-based devices. Mostly, skin or tendons are used for the preparation of collagen. The collagen in skin has a very low hydroxyallysine cross-linking. Indeed, collagen in skin has a short half-life. Tendons show various levels of hydroxyallysine cross-links, depending on the anatomical position of the tendon (see e.g. R. A. Bank et al., 1999, Arthr. Rheum., 58: 35–41). The collagen in tendon shows a much higher half-life. Bone shows intermediate levels of hydroxyallysine crosslinks. The amount of hydroxyallysine crosslinks further depends on bone type (cortical or trabecular) and skeletal site (see e.g. L. Knott & A. J. Bailey, 1999, British Poultry Science, 40: 371–379). By mixing the collagen derived from tissues containing low and high hydroxyallysine crosslinks in various ratios, collagen compositions are obtained that can be used for the manufacturing of collagenous matrices showing increased or decreased turnover times.

Example 5

Figure 6:
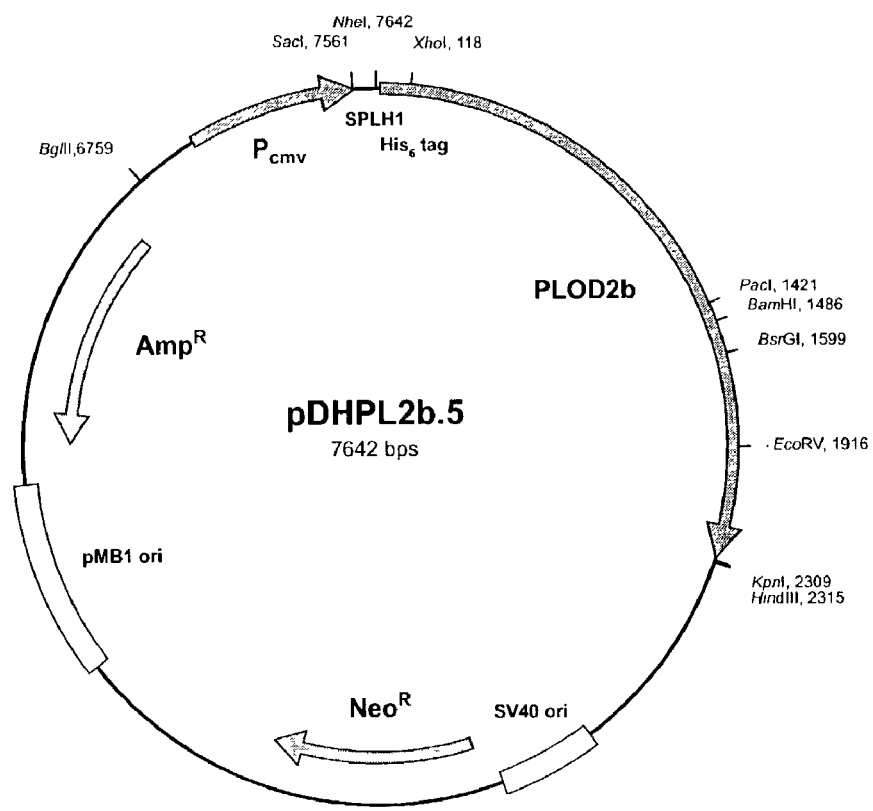
FIG. 6 is a graph showing the construct pDHPL2b.5 derived from the pMOSBlue vector used for the expression of recombinant PLOD2B in mammalian cells.

Expression of Recombinant PLOD2 in Cells to Enhance Lysyl Hydroxylation Levels in Telopeptides The human PLOD1 signal peptide sequence followed by a $His_6$ tag sequence was linked to the cDNA sequence of human PLOD2B starting from the likely amino-terminal end of the molecule. Four overlapping oligonucleotides, covering the nucleotide sequence for the PLOD1 signal peptide and a $His_6$ tag flanked by NheI and BamHI restriction sites, were annealed and the protruding 5' ends were filled in by cloned pfu polymerase (Stratagene). The resulting double-stranded, blunt-ended product was ligated to the EcoRV site of the pMOSBlue vector (Amersham). The human PLOD2B cDNA sequence covering nucleotides 76 to 2283 was cloned into the BamHI/KpnI sites of the construct. Finally, an expression construct (FIG. 6) was created by cloning the PLOD2B cDNA sequence with the PLOD1 signal peptide into the NheI/KpnI site of pcDNA3.1(−) (Invitrogen). A similar construct for splice variant PLOD2A, lacking exon 13A, was obtained by replacing a PacI/BsrGI fragment in the PLOD2B nucleotide sequence for the same fragment from the PLOD2A sequence. The expression constructs, called pDHPL2b.5 and pDHPL2a.4, were confirmed by sequencing. The recombinant proteins contain a $His_6$ tag at the N-terminus after signal peptide cleavage. HEK293 cells were cultured in DMEM supplemented with 10% FBS in 5% $CO_2$ until they reached confluency. For transfection cells were plated in 10 $cm^2$ wells at such a density that 70% confluence was reached after 16 hrs of incubation at 37° C. Two hours prior to transfection, fresh medium was added to the cells. The cells were transfected with a total of 1 μg of each plasmid using the lipid-based FuGENE™ 6 transfection reagent (Roche Molecular Biochemicals, Indianapolis, Ind., USA) in a ratio of 1:4 (μg DNA: μl FuGENE). To obtain stable HEK293 clones expressing TLH the cells were diluted 100 times 24 hours after transfection and plated in 10 $cm^2$ wells in selective medium containing 700 μg/ml geneticine (Invitrogen). After two weeks culturing in selective medium single clones were picked and screened for TLH expression by Western blotting. Considerable amounts of telopeptide lysyl hydroxylase were observed in both the cytosol and in the culture medium.

The same construct can be used to transfect collagen-producing cells in order to obtain cells that constitutively express telopeptide lysyl hydroxylase encoded by PLOD2. By doing so, collagen is secreted showing high levels of hydroxylysine in the telopeptides, being the molecular basis for the generation of collagen matrices with enhanced stability against proteinases. The secreted collagen can be purified by a variety of methods, such as those described by D. K. Furuto & E. J. Miller (1987, Methods Enzymol., 144: 41–61), and used for the preparation of scaffolds.

Example 6

Stimulation of Endogenous PLOD2 Expression in Cells to Enhance Lysyl Hydroxylation Levels in Telopeptides Human skin fibroblasts were cultured in 25 $cm^2$ flasks in DMEM (Gibco) supplemented with 10% FBS in 5% $CO_2$. At near confluency the fibroblasts and myofibroblasts were incubated for 50 hours in medium containing 1, 5 or 10 nM human recombinant TGF-β1, -β2 or -β3. As a control, human skin fibroblasts were incubated for 50 hours in medium without the addition of TGF-β. At the end of the incubation period, the cells were washed with PBS and lysed with 600 μl RLT-buffer (RNeasy kit, Qiagen). RNA was isolated following the manufacturers protocol and subsequently reverse transcribed into cDNA (first strand cDNA synthesis kit, Roche Molecular Biochemicals). The levels of PLOD2B mRNA in the untreated and TGF-β treated cells were quantified using real-time PCR as described in example 8.

Figure 9:
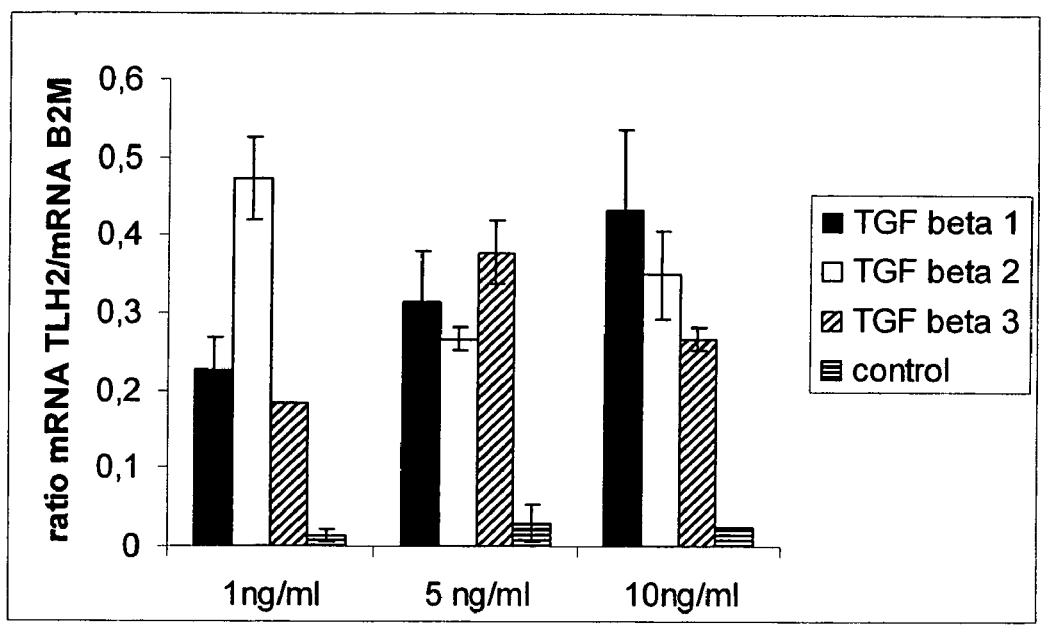
FIG. 9 is a graph showing that the expression of PLOD2B is increased in fibroblasts by adding TGF-β to the culture medium.

FIG. 9 shows that treatment of fibroblasts with TGF-β1, -β2 or -β3 increases the PLOD2B mRNA levels about 20-fold. TGF-β is thus an example of an agent that increases PLOD2B mRNA expression and can thus be used to increase cross-linking derived from the hydroxyallysine pathway. Such collagen can be purified and subsequently be used for the preparation of collagen scaffolds showing an increased resistance towards proteinases.

Example 7

Inhibition of Teloptide Lysyl Hydroxylase Activity Levels in Cells to Decrease Lysyl Hydroxylation Levels in Telopeptides Chondrocytes from the metacarpophalangeal joint of calves (12–14 months old, local slaughterhouse) were isolated by collagenase digestion: cartilage slices were minced and digested overnight at 37° C. in 0.14% (w/v) collagenase (Worthington CLS2) in Dulbecco's modified Eagle's medium (DMEM). After filtration of the suspension, cells were washed suspended in 1.2% (w/v) alginate (Keltone LVCR) in 0.9% NaCl at a density of $4 \times 10^6$ cells/ml, which was passed dropwise through a 22-gauge needle into 102 mM $CaCl_2$. After 10 min of polymerization, beads were washed in 0.9% (w/v) NaCl (three times) and finally in complete medium: DMEM-Glutamax (Gibco BRL) supplemented with 100 U/ml of penicillin/streptomycin, 10% (v/v) foetal calf serum and 50 µg/ml ascorbic acid. The cells were cultured at 10 beads per 0.5 ml medium in a humid atmosphere of 5% $CO_2$ in air at 37° C.; the medium was refreshed twice weekly. Minoxidil was dissolved in complete medium and added to the culture after 7 days of preculture under control conditions. Harvested beads were washed with 0.9% NaCl containing 10 mM $CaCl_2$ and hydrolyzed in 900 µl 6 M HCl at 108° C. for 20–24 h. An aliqout of the hydrolysate was subjected to amino acid analysis as described by R. A. Bank et al. [1996, Anal. Biochem., 260: 167–176]. Based on hydroxyproline levels, amounts of collagen were calculated, assuming 300 hydroxyproline residues/triple helix. Another aliquot was subjected to crosslink analysis as described by B. Beekman et al. [1997, Exp. Cell Res., 237: 135–141]. Crosslinks were expressed as amount of residues per collagen molecule.

The amount of pyridinolines (HP and LP) in alginate beads cultured in the presence of 1.0 mM or 2.0 mM minoxidil was in mean around 0.15 residues/collagen molecule after a culture period of 20–50 days, whereas the amount of pyridinolines in cultures treated with 0.3 mM minoxidil was in said culture period in mean 0.38 residues/collagen molecule. This shows that increased concentrations of minoxidil reduces the lysyl hydroxylation level of the telopeptides most likely by means of inhibiting the expression of PLOD2.

To substantiate that minoxidil suppresses the expression of PLOD2, human skin fibroblasts and myofibroblasts were cultured in 25 $cm^2$ flasks in DMEM (Gibco) supplemented with 10% FBS in 5% $CO_2$. At near confluency the fibroblasts and myofibroblasts were incubated for 41 hours in medium containing 1 mM minoxidil. Minoxidil was dissolved at room temperature in medium with 10% FBS for 8 hours which was filtered prior to use. As a control both cell types were incubated for 41 hours in medium without minoxidil. At the end of the incubation period, the cells were washed with PBS and lysed with 600 µl RLT-buffer (RNeasy kit, Qiagen). RNA was isolated following the manufacturers protocol and subsequently reverse transcribed into cDNA (first strand cDNA synthesis kit, Roche Molecular Biochemicals). The levels of PLOD2B mRNA in the untreated and minoxidil-treated cells were quantified using real-time PCR as described in example 8.

Figure 8:
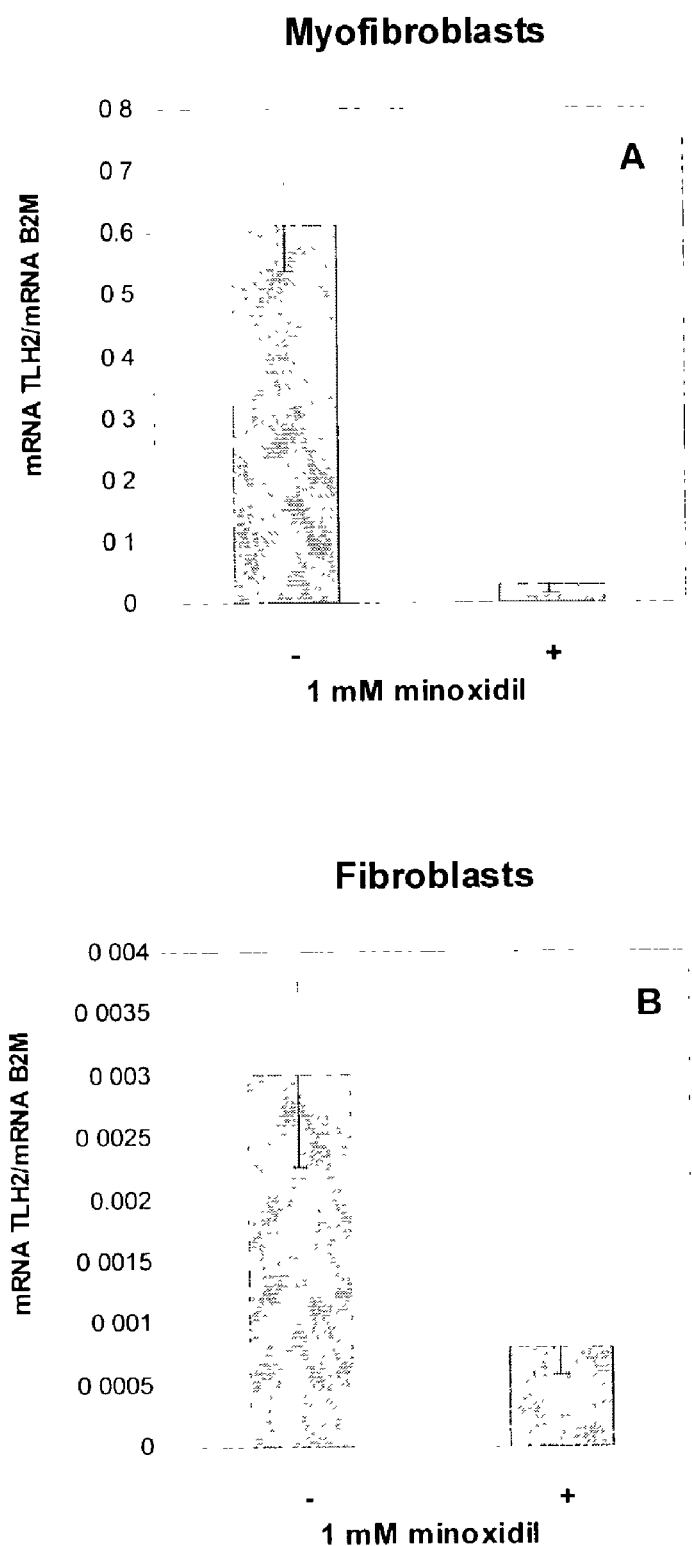
FIG. 8 is a graph showing that the expression of PLOD2B is inhibited in fibroblasts and myofibroblasts by adding minoxidil to the culture medium.

FIG. 8 shows that treatment of myofibroblasts with minoxidil reduces the PLOD2B mRNA levels about 15-fold. The PLOD2B mRNA levels in fibroblasts is much lower than in myofibroblasts (see example 8), but still a 4-fold reduction in mRNA levels can be measured when these cells are cultured in minoxidil containing medium. Minoxidil is thus an example of an inhibitor of PLOD2B mRNA expression and can be used to reduce the cross-links derived from the hydroxyallysine pathway. Lysyl oxidase levels were not affected by the minoxidil treatment.

Example 8

Inhibition of Telopeptide Lysyl Hydroxylase Using Antisense Oligonucleotides to Decrease Lysyl Hydroxylation Levels in Telopeptides The expression of TLH can be downregulated at the post-transcriptional level by degrading the PLOD2 mRNA using antisense oligonucleotides (AONs). We designed 10 phosphorothioated AONs and tested in vitro their potential for duplex formation with the PLOD2 mRNA and subsequent degradation of the mRNA by RNase H. Non-denatured RNA from $1 \times 10^4$ myofibroblasts was incubated for 4 h with 8 µM AON at 37° C. in 15 mM TrisHCI, 2 mM $MgCl_2$, 50 mM KCl pH 8.0 in a final volume of 25 µl. Degradation of the duplexed mRNA was performed by adding 1 µd 10 mM DTT and 2 u RNase H and incubating the mixture for an additional 20 min at 37° C. The remaining RNA was reverse transcribed and subjected to PCR with the primers: hPLOD2bRTF (5' TTAAAGGAAAGACACTC-CGATCAGAGATGA 3') (SEQ ID NO:44) and hPLOD2aRTR4 (5' TAGCCTTCCAAATTCATGTC-TATTAGAAATGTA 3') (SEQ ID NO: 45), which have been chosen such that PLOD2a and PLOD2b cDNA amplification can be distinguished in a single reaction. Two AONs out of ten were able to decrease the amount of PLOD2 mRNA to an undetectable level. One recognizes both PLOD2a and PLOD2b mRNA and has the following sequence: 5' CCCATATTCGGCCCTC 3' (SEQ ID NO: 46) (-11-5 nt in the PLOD2 cDNA sequence) covering the start codon. The second AON with the sequence 5' TTCCCTTTGTAAAGT 3' (SEQ ID NO: 47) (1500–1514 nt in the PLOD2b cDNA sequence) is specific for PLOD2b mRNA and recognizes the extra exon in the PLOD2b sequence. These two AONs are promising for treating for instance myofibroblasts in order to decrease their PLOD2 mRNA levels and as a consequence the amount of HP and LP crosslinks in the extracellular matrix formed by these cells.

Example 9

Real-Time PCR to Measure PLOD2 mRNA Levels

RNA, obtained from cultured human skin fibroblasts and cultured human myofibroblast, was isolated using the RNeasy kit (Qiagen). To remove any genomic DNA in the RNA sample, a Dnase treatment was carried out, using RQ1 Rnase-free Dnase (Promega). RNA was then reverse transcripted into cDNA and subjected to real time PCR amplification.

Real time PCR amplification of PLOD2 and β2-microglobulin was performed, using specific primers (PLOD2 forward primer: 5' TTAAAGGAAAGACACTCCGATCA-GAGATGA 3' (SEQ ID NO:48) PLOD2 reverse primer: 5' AATGTTTCCGGAGTAGGGGAGTCTTTTT 3' (SEQ ID NO:49)β2-microglobulin forward primer; 5' ATCCAAAT-GCGGCATCTTCAAACTCC 3 (SEQ ID NO:50)β32-microglobulin reverse primer 5' ATCCAAATGCGGCATCT-TCAAACCTC 3') (SEQ ID NO:51) and specific molecular beacons PLOD2: 5' FAM-cgtgcgCGTGATAAACTGGATC-CTGATATGGCTCTT (SEQ ID NO:52) cgcacg-DABCYL 3 '; β2-microglobulin: 5'HEX-cgtgcCCTGCCGTGTGAAC-CATGTGACTTTG (SEQ ID NO:53) gcacg-DABCYL 3'). PLOD2 was amplified in a multiplex PCR together with β2-microglobulin in a total reaction volume of 25µl, containing 1×PCR buffer (Applied Biosystems), 0.4 mM of each dNTP, 3.5 mM $Mg^{2+}$, 250 nM of each target primer, 100 nM of each primer for µ2microglobulin and 1 unit Amplitaq Gold polymerase (Applied Biosystems). PCR was performed in a ABI PRISM® 7700 Sequence Detection System and consisted of a 5 minute interval at 95° C., followed by 40 cycles of 95° C. for 30 seconds, 56° C. for 40 seconds and 72° C. for 30 seconds. Data was analysed using sequence detector V1.7 software.

FIG. 5 shows that myofibroblast-like cells show in mean a 40-fold increase of PLOD2 mRNA levels compared to fibroblasts. Myofibroblasts play a key role in fibrotic processes [C. Badid et al., 2000, Histol. Histopathol., 15: 269–280]. The data indicate that telopeptide lysyl hydroxylase is highly upregulated in fibrotic tissues. This is further corroborated by our observation, that collagen from skin show very low levels of hydroxyallysine cross-links in collagen (0.02 HP residues per triple helix), whereas collagen laid down in tissues containing myofibroblasts show high levels of hydroxyallysine cross-links (0.45 HP residues per triple helix).

As hydroxylation of the telopeptide lysine is controlled by telopeptide lysyl hydroxylase, and as the collagen network containing hydroxyallysine cross-links is more resistant towards proteinases, it is clear that telopeptide lysyl hydroxylase is a key enzyme in fibrosis. The understanding that PLOD2 encodes telopeptide lysyl hydroxylase provides the skilled artisan with the necessary information for monitoring the onset and/or progression of fibrotic processes by measuring mRNA levels of PLOD2 and/or protein levels of telopeptide lysyl hydroxylase and/or activity levels of telopeptide lysyl hydroxylase.

Example 10

High Through-put Assay

A peptide containing a hydroxylatable lysine residue, such as biotin-Q-L-S-Y-G-Y-D-E-K-S-T-G-G-I-S-V-P, is dissolved at a concentration of 1 nmol per 0.1 ml PBS. This was added to a mixture of 0.05 ml bovine serum albumin (5 mg albumin Sigma A-7888/ml PBS), 0.05 ml catalase (3.9 ml PBS +0.1 ml catalase suspesion from Sigma C-100), 0.1 ml 1 mM dithiothreitol, 0.05 ml 20 mM ascorbic acid, 0.05 ml 1 mM ferrous sulfate, 0.1 ml PBS containing the compound to be tested for its inhibitory properties towards telopeptide lysyl hydroxylase, 0.1 ml PBS containing telopeptidase lysyl hydroxylase activity and 0.05 ml α-ketoglutarate. The mixture is incubated for 3 hours at 30° C. An aliquot of the mixture (100 µl) is allowed to bind to the streptavidin coated on 96 wells plate (Pierce) at room temperature for 15 min. The non-bonded fractions were washed away three times with wash buffer (5% Tween-20 in PBS). The bonded peptides are allowed to react with 100 µl of 0.36 µg/ml $NalO_4$ in 0.025 M phosphate pH 7.0 for 10 min. An additional 3 washing steps are carried out before adding 100 µl of 3.1 µg/ml Texas Red hydrazide in 0.1 M sodium acetate/acetonitril (1:2) pH 4.5. The solution is gently shaken for 2 h at room temperature. After a nine-fold wash step with wash buffer, fluorescence is measured (e.g. with a Cytofluor) at an excitation and emission wave length of 580 nm and 605 nm, respectively. Inhibition of the activity of telopeptide lysyl hydroxylase by the compound in question results in a decrease in the amount of fluorescence, as lysine cannot be converted into an aldehyde in the protocol described above.

Various other hydrazides can be used, such as Lucifer yellow, BODIPYL or Cascade Blue. Instead of biotin, a StrepFlag sequence can be used for binding to the streptavidin. Alternative, other chemistry formats can be chosen, such as a His-tagged peptide in combination with a $Ni^{2+}$ carrier, or a SAMA peptide in combination with maleimide-coated plates.

The invention claimed is:

1. A method for obtaining an ex vivo collagenous matrix which comprises cross-linked collagen molecules by controlling the ratio of hydroxyallysine cross-links to allysine cross-links in the ex vivo collagenous matrix, thereby controlling the resistance of said collagenous matrix against proteolytic degradation.

2. The method of claim 1 wherein the ratio of hydroxyallysine cross-links to allysine cross-links in the collagenous matrix is controlled by controlling the lysyl hydroxylation level of the collagen telopeptides.

3. The method of claim 2 wherein the lysyl hydroxylation level of the collagen telopeptides is controlled by controlling the level of telopeptide lysyl hydroxylase activity.

4. The method of claim 3 wherein the level of telopeptide lysyl hydroxylase activity is controlled by controlling the expression of a PLOD2 gene or by controlling the telopeptide lysyl hydroxylase activity of a PLOD2 expression product.

5. The method of claim 1 comprising obtaining collagen from tissues which show an increased ratio of hydroxyallysine cross-links to allysine cross-links and using said collagen to prepare a collagenous matrix with an increased resistance against proteolytic degradation.

6. The method of claim 1 comprising obtaining collagen from tissues which predominantly show allysine cross-links and using said collagen for preparing a collagenous matrix, wherein a collagenous matrix with an increased resistance against proteolytic degradation is obtained by admixing collagen obtained from tissues which show an increased ratio of hydroxyallysine cross-links to allysine cross-links and using said collagen to prepare a collagenous matrix with an increased resistance against proteolytic degradation.

7. The method of claim 1 comprising culturing cells producing collagen with telopeptides having an increased ratio of hydroxylysine to lysine residues and using the collagen produced for preparing a collagenous matrix having an increased resistance against proteolytic degradation due to an increased ratio of hydroxyallysine cross-links to allysine cross-links.

8. The method of claim 7 wherein said collagen-producing cells comprise a recombinant, constitutively expressed PLOD2 gene.

9. The method of claim 7 wherein said collagen-producing cells are cultured in the presence of a composition which stimulates the expression of a PLOD2 gene.

10. The method of claim 1 comprising obtaining collagen from tissues which show a decreased ratio of hydroxyallysine cross-links to allysine cross-links and using said collagen to prepare a collagenous matrix with a decreased resistance against proteolytic degradation.

11. The method of claim 1 comprising obtaining collagen from tissues which predominantly show hydroxyallysine cross-links and using said collagen for preparing a collagenous matrix, wherein a collagenous matrix with a decreased resistance against proteolytic degradation is obtained by admixing collagen obtained from tissues which show a decreased ratio of hydroxyallysine cross-links to allysine cross-links and using said collagen to prepare a collagenous matrix with a decreased resistance against proteolytic degradation.

12. The method of claim 1 comprising culturing cells producing collagen with telopeptides having a decreased ratio of hydroxylysine to lysine residues and using the collagen produced for preparing a collagenous matrix having a decreased resistance against proteolytic degradation due to a decreased ratio of hydroxyallysine cross-links to allysine cross-links.

13. The method of claim 12 wherein said collagen-producing cells are cultured in the presence of a composition which inhibits the activity or production of PLOD2-encoded telopeptide lysyl hydroxylase.

14. The method of claim 13 wherein said composition does not affect the level of lysyl oxidase.

* * * * *

SEQUENCE LISTING

<160> NUMBER OF SEQ ID NOS: 59

<210> SEQ ID NO 1
<211> LENGTH: 8
<212> TYPE: PRT
<213> ORGANISM: Homo sapiens

<400> SEQUENCE: 1

Gly Gly Tyr Glu Asn Val Pro Thr
1               5

<210> SEQ ID NO 2
<211> LENGTH: 9
<212> TYPE: PRT
<213> ORGANISM: Artificial Sequence
<220> FEATURE:
<223> OTHER INFORMATION: synthetic peptide sequence

```
<400> SEQUENCE: 2

Ile Lys Gly Ile Lys Gly Ile Lys Gly
1               5

<210> SEQ ID NO 3
<211> LENGTH: 12
<212> TYPE: PRT
<213> ORGANISM: Artificial Sequence
<220> FEATURE:
<223> OTHER INFORMATION: synthetic peptide sequence

<400> SEQUENCE: 3

Ala Arg Gly Ile Lys Gly Ile Arg Gly Phe Ser Gly
1               5                   10

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
ctcccaaagc taagtgcagg                                              20

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
gtctctgcgt tctcgcgaga                                              20

<210> SEQ ID NO 6
<211> LENGTH: 23
<212> TYPE: DNA
<213> ORGANISM: Artificial Sequence
<220> FEATURE:
<223> OTHER INFORMATION: primer

<400> SEQUENCE: 6
tgaggtctca attactgtag tga                                          23

<210> SEQ ID NO 7
<211> LENGTH: 23
<212> TYPE: DNA
<213> ORGANISM: Artificial Sequence
<220> FEATURE:
<223> OTHER INFORMATION: primer

<400> SEQUENCE: 7
gtactgttca agttgatgat gtc                                          23

<210> SEQ ID NO 8
<211> LENGTH: 24
<212> TYPE: DNA
<213> ORGANISM: Artificial Sequence
<220> FEATURE:
<223> OTHER INFORMATION: primer

<400> SEQUENCE: 8
atggtttatg tgcctagatt ctga                                         24
```

<210> SEQ ID NO 9
<211> LENGTH: 21
<212> TYPE: DNA
<213> ORGANISM: Artificial Sequence
<220> FEATURE:
<223> OTHER INFORMATION: primer

<400> SEQUENCE: 9
ttctttcatg gtgagctgtg a                                        21

<210> SEQ ID NO 10
<211> LENGTH: 22
<212> TYPE: DNA
<213> ORGANISM: Artificial Sequence
<220> FEATURE:
<223> OTHER INFORMATION: primer

<400> SEQUENCE: 10
gcaactatcg cagtttctac ct                                       22

<210> SEQ ID NO 11
<211> LENGTH: 22
<212> TYPE: DNA
<213> ORGANISM: Artificial Sequence
<220> FEATURE:
<223> OTHER INFORMATION: primer

<400> SEQUENCE: 11
cacatacaca cacagacaca cg                                       22

<210> SEQ ID NO 12
<211> LENGTH: 23
<212> TYPE: DNA
<213> ORGANISM: Artificial Sequence
<220> FEATURE:
<223> OTHER INFORMATION: primer

<400> SEQUENCE: 12
taaaggaata tacctgctgc aga                                      23

<210> SEQ ID NO 13
<211> LENGTH: 23
<212> TYPE: DNA
<213> ORGANISM: Artificial Sequence
<220> FEATURE:
<223> OTHER INFORMATION: primer

<400> SEQUENCE: 13
tttcaagtgt tagagaactg cca                                      23

<210> SEQ ID NO 14
<211> LENGTH: 23
<212> TYPE: DNA
<213> ORGANISM: Artificial Sequence
<220> FEATURE:
<223> OTHER INFORMATION: primer

<400> SEQUENCE: 14
tctaagattt ctaggctaca ggc                                      23

<210> SEQ ID NO 15
<211> LENGTH: 23
<212> TYPE: DNA
<213> ORGANISM: Artificial Sequence
<220> FEATURE:
<223> OTHER INFORMATION: primer

```
<400> SEQUENCE: 15
cagaaaagta tgctagagaa cca                                          23

<210> SEQ ID NO 16
<211> LENGTH: 23
<212> TYPE: DNA
<213> ORGANISM: Artificial Sequence
<220> FEATURE:
<223> OTHER INFORMATION: primer

<400> SEQUENCE: 16
caggtttgtt gaatgagctt tct                                          23

<210> SEQ ID NO 17
<211> LENGTH: 21
<212> TYPE: DNA
<213> ORGANISM: Artificial Sequence
<220> FEATURE:
<223> OTHER INFORMATION: primer

<400> SEQUENCE: 17
ggggcagtgg tttatctcct a                                            21

<210> SEQ ID NO 18
<211> LENGTH: 21
<212> TYPE: DNA
<213> ORGANISM: Artificial Sequence
<220> FEATURE:
<223> OTHER INFORMATION: primer

<400> SEQUENCE: 18
agaatacctg agagagcggg t                                            21

<210> SEQ ID NO 19
<211> LENGTH: 22
<212> TYPE: DNA
<213> ORGANISM: Artificial Sequence
<220> FEATURE:
<223> OTHER INFORMATION: primer

<400> SEQUENCE: 19
cagttgagtg tcagtgctat ct                                           22

<210> SEQ ID NO 20
<211> LENGTH: 23
<212> TYPE: DNA
<213> ORGANISM: Artificial Sequence
<220> FEATURE:
<223> OTHER INFORMATION: primer

<400> SEQUENCE: 20
ataagcatat tcagaaccag gca                                          23

<210> SEQ ID NO 21
<211> LENGTH: 22
<212> TYPE: DNA
<213> ORGANISM: Artificial Sequence
<220> FEATURE:
<223> OTHER INFORMATION: primer

<400> SEQUENCE: 21
tcatcaattc tgaggtgcac ca                                           22

<210> SEQ ID NO 22
```

```
<211> LENGTH: 23
<212> TYPE: DNA
<213> ORGANISM: Artificial Sequence
<220> FEATURE:
<223> OTHER INFORMATION: primer

<400> SEQUENCE: 22
agcagatgat ataccacatt gga                                              23

<210> SEQ ID NO 23
<211> LENGTH: 19
<212> TYPE: DNA
<213> ORGANISM: Artificial Sequence
<220> FEATURE:
<223> OTHER INFORMATION: primer

<400> SEQUENCE: 23
agacagggat tccagggt                                                    19

<210> SEQ ID NO 24
<211> LENGTH: 22
<212> TYPE: DNA
<213> ORGANISM: Artificial Sequence
<220> FEATURE:
<223> OTHER INFORMATION: primer

<400> SEQUENCE: 24
aagggctgtt ggatgaatga ac                                               22

<210> SEQ ID NO 25
<211> LENGTH: 23
<212> TYPE: DNA
<213> ORGANISM: Artificial Sequence
<220> FEATURE:
<223> OTHER INFORMATION: primer

<400> SEQUENCE: 25
cttccttgtg aggattacag att                                              23

<210> SEQ ID NO 26
<211> LENGTH: 21
<212> TYPE: DNA
<213> ORGANISM: Artificial Sequence
<220> FEATURE:
<223> OTHER INFORMATION: primer

<400> SEQUENCE: 26
gccaccgtgc ccaaccatat t                                                21

<210> SEQ ID NO 27
<211> LENGTH: 23
<212> TYPE: DNA
<213> ORGANISM: Artificial Sequence
<220> FEATURE:
<223> OTHER INFORMATION: primer

<400> SEQUENCE: 27
ggaacaccaa ctcacataat aca                                              23

<210> SEQ ID NO 28
<211> LENGTH: 20
<212> TYPE: DNA
<213> ORGANISM: Artificial Sequence
<220> FEATURE:
<223> OTHER INFORMATION: primer

<400> SEQUENCE: 28
```
tgatatccag ccaggtgaca                                               20

<210> SEQ ID NO 29
<211> LENGTH: 24
<212> TYPE: DNA
<213> ORGANISM: Artificial Sequence
<220> FEATURE:
<223> OTHER INFORMATION: primer

<400> SEQUENCE: 29
ccaaatggac ataacaaagg aaag                                          24

<210> SEQ ID NO 30
<211> LENGTH: 22
<212> TYPE: DNA
<213> ORGANISM: Artificial Sequence
<220> FEATURE:
<223> OTHER INFORMATION: primer

<400> SEQUENCE: 30
aaaggctatc actctgctga gg                                            22

<210> SEQ ID NO 31
<211> LENGTH: 23
<212> TYPE: DNA
<213> ORGANISM: Artificial Sequence
<220> FEATURE:
<223> OTHER INFORMATION: primer

<400> SEQUENCE: 31
attccactta catctactgc aga                                           23

<210> SEQ ID NO 32
<211> LENGTH: 23
<212> TYPE: DNA
<213> ORGANISM: Artificial Sequence
<220> FEATURE:
<223> OTHER INFORMATION: primer

<400> SEQUENCE: 32
ccactgaact taacccaatg aat                                           23

<210> SEQ ID NO 33
<211> LENGTH: 22
<212> TYPE: DNA
<213> ORGANISM: Artificial Sequence
<220> FEATURE:
<223> OTHER INFORMATION: primer

<400> SEQUENCE: 33
gttggctact gcatacgcaa ac                                            22

<210> SEQ ID NO 34
<211> LENGTH: 23
<212> TYPE: DNA
<213> ORGANISM: Artificial Sequence
<220> FEATURE:
<223> OTHER INFORMATION: primer

<400> SEQUENCE: 34
gtagaacata actaagttcc ctc                                           23

<210> SEQ ID NO 35
<211> LENGTH: 21
<212> TYPE: DNA

<213> ORGANISM: Artificial Sequence
<220> FEATURE:
<223> OTHER INFORMATION: primer

<400> SEQUENCE: 35
aggattccaa gtggtcttgg g                                       21

<210> SEQ ID NO 36
<211> LENGTH: 21
<212> TYPE: DNA
<213> ORGANISM: Artificial Sequence
<220> FEATURE:
<223> OTHER INFORMATION: primer

<400> SEQUENCE: 36
cacagtgaca caccaactgg t                                       21

<210> SEQ ID NO 37
<211> LENGTH: 22
<212> TYPE: DNA
<213> ORGANISM: Artificial Sequence
<220> FEATURE:
<223> OTHER INFORMATION: primer

<400> SEQUENCE: 37
acgcaaacac acagatgact ga                                      22

<210> SEQ ID NO 38
<211> LENGTH: 22
<212> TYPE: DNA
<213> ORGANISM: Artificial Sequence
<220> FEATURE:
<223> OTHER INFORMATION: primer

<400> SEQUENCE: 38
ctggtgtgag acagtatctc at                                      22

<210> SEQ ID NO 39
<211> LENGTH: 22
<212> TYPE: DNA
<213> ORGANISM: Artificial Sequence
<220> FEATURE:
<223> OTHER INFORMATION: primer

<400> SEQUENCE: 39
ctccactttc acatcttctg tg                                      22

<210> SEQ ID NO 40
<211> LENGTH: 20
<212> TYPE: DNA
<213> ORGANISM: Artificial Sequence
<220> FEATURE:
<223> OTHER INFORMATION: primer

<400> SEQUENCE: 40
agaaacccgc ccaaactaat                                         20

<210> SEQ ID NO 41
<211> LENGTH: 22
<212> TYPE: DNA
<213> ORGANISM: Artificial Sequence
<220> FEATURE:
<223> OTHER INFORMATION: primer

<400> SEQUENCE: 41
gttcatgcca gtcattcatc ca                                      22

<210> SEQ ID NO 42
<211> LENGTH: 20
<212> TYPE: DNA
<213> ORGANISM: Artificial Sequence
<220> FEATURE:
<223> OTHER INFORMATION: sequence primer for exon 18 of PLOD2

<400> SEQUENCE: 42
ggtctttgca ggctattata                                           20

<210> SEQ ID NO 43
<211> LENGTH: 19
<212> TYPE: DNA
<213> ORGANISM: Artificial Sequence
<220> FEATURE:
<223> OTHER INFORMATION: sequence primer for exon 19 of PLOD2

<400> SEQUENCE: 43
gctcaaatga cataatttg                                            19

<210> SEQ ID NO 44
<211> LENGTH: 30
<212> TYPE: DNA
<213> ORGANISM: Artificial Sequence
<220> FEATURE:
<223> OTHER INFORMATION: primer hPLOD2bRTF

<400> SEQUENCE: 44
ttaaaggaaa gacactccga tcagagatga                                30

<210> SEQ ID NO 45
<211> LENGTH: 33
<212> TYPE: DNA
<213> ORGANISM: Artificial Sequence
<220> FEATURE:
<223> OTHER INFORMATION: primer hPLOD2aRTR4

<400> SEQUENCE: 45
tagccttcca aattcatgtc tattagaaat gta                            33

<210> SEQ ID NO 46
<211> LENGTH: 16
<212> TYPE: DNA
<213> ORGANISM: Artificial Sequence
<220> FEATURE:
<223> OTHER INFORMATION: antisense oligonucleotide specific for PLOD2

<400> SEQUENCE: 46
cccatattcg gccctc                                               16

<210> SEQ ID NO 47
<211> LENGTH: 15
<212> TYPE: DNA
<213> ORGANISM: Artificial Sequence
<220> FEATURE:
<223> OTHER INFORMATION: antisense oligonucleotide specific for PLOD2

<400> SEQUENCE: 47
ttccctttgt aaagt                                                15

<210> SEQ ID NO 48
<211> LENGTH: 30
<212> TYPE: DNA
<213> ORGANISM: Artificial Sequence
<220> FEATURE:

```
<223> OTHER INFORMATION: PLOD2 forward primer

<400> SEQUENCE: 48
ttaaaggaaa gacactccga tcagagatga                                    30

<210> SEQ ID NO 49
<211> LENGTH: 28
<212> TYPE: DNA
<213> ORGANISM: Artificial Sequence
<220> FEATURE:
<223> OTHER INFORMATION: PLOD2 reverse primer

<400> SEQUENCE: 49
aatgtttccg gagtagggga gtcttttt                                      28

<210> SEQ ID NO 50
<211> LENGTH: 31
<212> TYPE: DNA
<213> ORGANISM: Artificial Sequence
<220> FEATURE:
<223> OTHER INFORMATION: beta2-microglobulin forward primer

<400> SEQUENCE: 50
tcttgtacta cactgaattc accccactg a                                   31

<210> SEQ ID NO 51
<211> LENGTH: 26
<212> TYPE: DNA
<213> ORGANISM: Artificial Sequence
<220> FEATURE:
<223> OTHER INFORMATION: beta2-microglobulin reverse primer

<400> SEQUENCE: 51
atccaaatgc ggcatcttca aacctc                                        26

<210> SEQ ID NO 52
<211> LENGTH: 42
<212> TYPE: DNA
<213> ORGANISM: Artificial Sequence
<220> FEATURE:
<223> OTHER INFORMATION: PLOD2-specific beacon probe

<400> SEQUENCE: 52
cgtgcgcgtg ataaactgga tcctgatatg gctcttcgca cg                      42

<210> SEQ ID NO 53
<211> LENGTH: 36
<212> TYPE: DNA
<213> ORGANISM: Artificial Sequence
<220> FEATURE:
<223> OTHER INFORMATION: beta2-microglobulin specific beacon probe

<400> SEQUENCE: 53
cgtgccctgc cgtgtgaacc atgtgacttt ggcacg                             36

<210> SEQ ID NO 54
<211> LENGTH: 17
<212> TYPE: PRT
<213> ORGANISM: Artificial Sequence
<220> FEATURE:
<223> OTHER INFORMATION: substrate peptide for telopeptide lysyl
      hydroxylase enzyme

<400> SEQUENCE: 54

Gln Leu Ser Tyr Gly Tyr Asp Glu Lys Ser Thr Gly Gly Ile Ser Val
1               5                  10                  15
```

Pro

<210> SEQ ID NO 55
<211> LENGTH: 12
<212> TYPE: DNA
<213> ORGANISM: Artificial Sequence
<220> FEATURE:
<223> OTHER INFORMATION: part of wild type PLOD2 sequence

<400> SEQUENCE: 55
tctggtggtt at                                                              12

<210> SEQ ID NO 56
<211> LENGTH: 12
<212> TYPE: DNA
<213> ORGANISM: Artificial Sequence
<220> FEATURE:
<223> OTHER INFORMATION: part of PLOD2 sequence of Bruck syndrome
      patient

<400> SEQUENCE: 56
tctgttggtt at                                                              12

<210> SEQ ID NO 57
<211> LENGTH: 12
<212> TYPE: DNA
<213> ORGANISM: Artificial Sequence
<220> FEATURE:
<223> OTHER INFORMATION: part of wild type PLOD2 sequence

<400> SEQUENCE: 57
tgtcccaact ga                                                              12

<210> SEQ ID NO 58
<211> LENGTH: 12
<212> TYPE: DNA
<213> ORGANISM: Artificial Sequence
<220> FEATURE:
<223> OTHER INFORMATION: part of PLOD2 sequence
<220> FEATURE:
<221> NAME/KEY: misc_feature
<222> LOCATION: (9)..(9)
<223> OTHER INFORMATION: "N" on pos. 9 stands for unknown nucleic acid

<400> SEQUENCE: 58
tgtcccaant ga                                                              12

<210> SEQ ID NO 59
<211> LENGTH: 12
<212> TYPE: DNA
<213> ORGANISM: Artificial Sequence
<220> FEATURE:
<223> OTHER INFORMATION: part of PLOD2 sequence of Bruck syndrome
      patient

<400> SEQUENCE: 59
tgtcccaatt ga                                                              12